(12) United States Patent
Grover

(10) Patent No.: US 8,043,849 B2
(45) Date of Patent: *Oct. 25, 2011

(54) THERMAL CYCLING DEVICE

(75) Inventor: Joel W. Grover, Pittsford, NY (US)

(73) Assignee: Thermal Gradient, Pittsford, NY (US)

( * ) Notice: Subject to any disclaimer, the term of this patent is extended or adjusted under 35 U.S.C. 154(b) by 1124 days.

This patent is subject to a terminal disclaimer.

(21) Appl. No.: 11/744,676

(22) Filed: May 4, 2007

(65) Prior Publication Data

US 2007/0202531 A1    Aug. 30, 2007

Related U.S. Application Data

(63) Continuation-in-part of application No. 10/906,546, filed on Feb. 24, 2005, now Pat. No. 7,618,811.

(60) Provisional application No. 60/547,036, filed on Feb. 24, 2004, provisional application No. 60/629,910, filed on Nov. 22, 2004, provisional application No. 60/746,550, filed on May 5, 2006.

(51) Int. Cl.
*C12M 1/34* (2006.01)
*C12M 3/00* (2006.01)
*C12M 1/00* (2006.01)
*C12M 1/22* (2006.01)

(52) U.S. Cl. ............... 435/303.1; 435/287.2; 435/288.7; 435/305.1

(58) Field of Classification Search ............... 435/287.2, 435/288.7, 305.1, 303.1
See application file for complete search history.

(56) References Cited

U.S. PATENT DOCUMENTS

| | | | |
|---|---|---|---|
| 5,176,203 A | 1/1993 | Larzul | |
| 5,587,128 A | 12/1996 | Wilding et al. | |
| 5,716,842 A | 2/1998 | Baier et al. | |
| 5,720,923 A | 2/1998 | Haff et al. | |
| 5,736,314 A | 4/1998 | Hayes et al. | |
| 5,779,977 A | 7/1998 | Haff et al. | |
| 5,792,430 A * | 8/1998 | Hamper | 422/131 |
| 5,827,480 A | 10/1998 | Haff et al. | |
| 5,897,842 A | 4/1999 | Dunn et al. | |
| 5,965,410 A | 10/1999 | Chow et al. | |
| 5,985,651 A | 11/1999 | Hunicke-Smith | |
| 6,033,880 A | 3/2000 | Haff et al. | |
| 6,054,263 A | 4/2000 | Danssaert et al. | |
| 6,132,996 A | 10/2000 | Hunicke-Smith | |
| 6,168,948 B1 | 1/2001 | Anderson et al. | |
| 6,174,675 B1 | 1/2001 | Chow et al. | |

(Continued)

FOREIGN PATENT DOCUMENTS

WO    WO 9941015 A1 *    8/1999

*Primary Examiner* — Michael Marcheschi
*Assistant Examiner* — Lydia Edwards
(74) *Attorney, Agent, or Firm* — John A. Artz; Dickinson Wright PLLC

(57) ABSTRACT

Multi-layer devices suitable for thermal cycling processes. The devices are particularly suitable for performing polymerase chain reactions (PCR). One embodiment includes a first conducting layer, a second conducting layer adjacent to the first layer, and a third conducting layer adjacent to the second layer opposite the first layer. Insulating layers are positioned between said three conducting layers. Continuous channels are formed within the layers. The channels can be formed in either the conducting layer or the insulating layers, or both. Other embodiments include two conducting layers. At least one integral or separate temperature source may be provided to maintain the conducting layers at various desired temperatures.

37 Claims, 11 Drawing Sheets

U.S. PATENT DOCUMENTS

| | | |
|---|---|---|
| 6,180,372 B1 | 1/2001 | Franzen |
| 6,261,431 B1 | 7/2001 | Mathies et al. |
| 6,284,525 B1 | 9/2001 | Mathies et al. |
| 6,303,343 B1 | 10/2001 | Kipf-Sill |
| 6,337,435 B1 | 1/2002 | Chu et al. |
| 6,375,817 B1 | 4/2002 | Taylor et al. |
| 6,428,987 B2 | 8/2002 | Franzen |
| 6,524,830 B2 | 2/2003 | Kopf-Sill |
| 6,534,009 B1 | 3/2003 | Yao |
| 6,537,799 B2 | 3/2003 | Chow et al. |
| 6,586,233 B2 | 7/2003 | Benett et al. |
| 6,673,593 B2 | 1/2004 | Mastromatteo et al. |
| 6,830,936 B2 | 12/2004 | Anderson et al. |
| 6,896,855 B1 * | 5/2005 | Köhler et al. ................ 422/191 |
| 7,618,811 B2 * | 11/2009 | Juncosa et al. ............. 435/287.2 |
| 2002/0022261 A1 | 2/2002 | Anderson et al. |
| 2003/0091477 A1 | 5/2003 | Paul et al. |
| 2003/0170883 A1 | 9/2003 | Martin et al. |
| 2003/0198962 A1 | 10/2003 | Chung et al. |
| 2004/0053290 A1 | 3/2004 | Terbrueggen et al. |
| 2004/0096958 A1 | 5/2004 | Pottathil et al. |
| 2004/0096961 A1 | 5/2004 | Huang et al. |
| 2004/0131345 A1 | 7/2004 | Kylberg et al. |
| 2004/0166569 A1 | 8/2004 | Marziali et al. |
| 2004/0197810 A1 | 10/2004 | Takenaka et al. |
| 2004/0209280 A1 | 10/2004 | Sundararajan et al. |
| 2004/0241048 A1 | 12/2004 | Shin et al. |
| 2007/0172395 A1 * | 7/2007 | Lim et al. ...................... 422/102 |

* cited by examiner

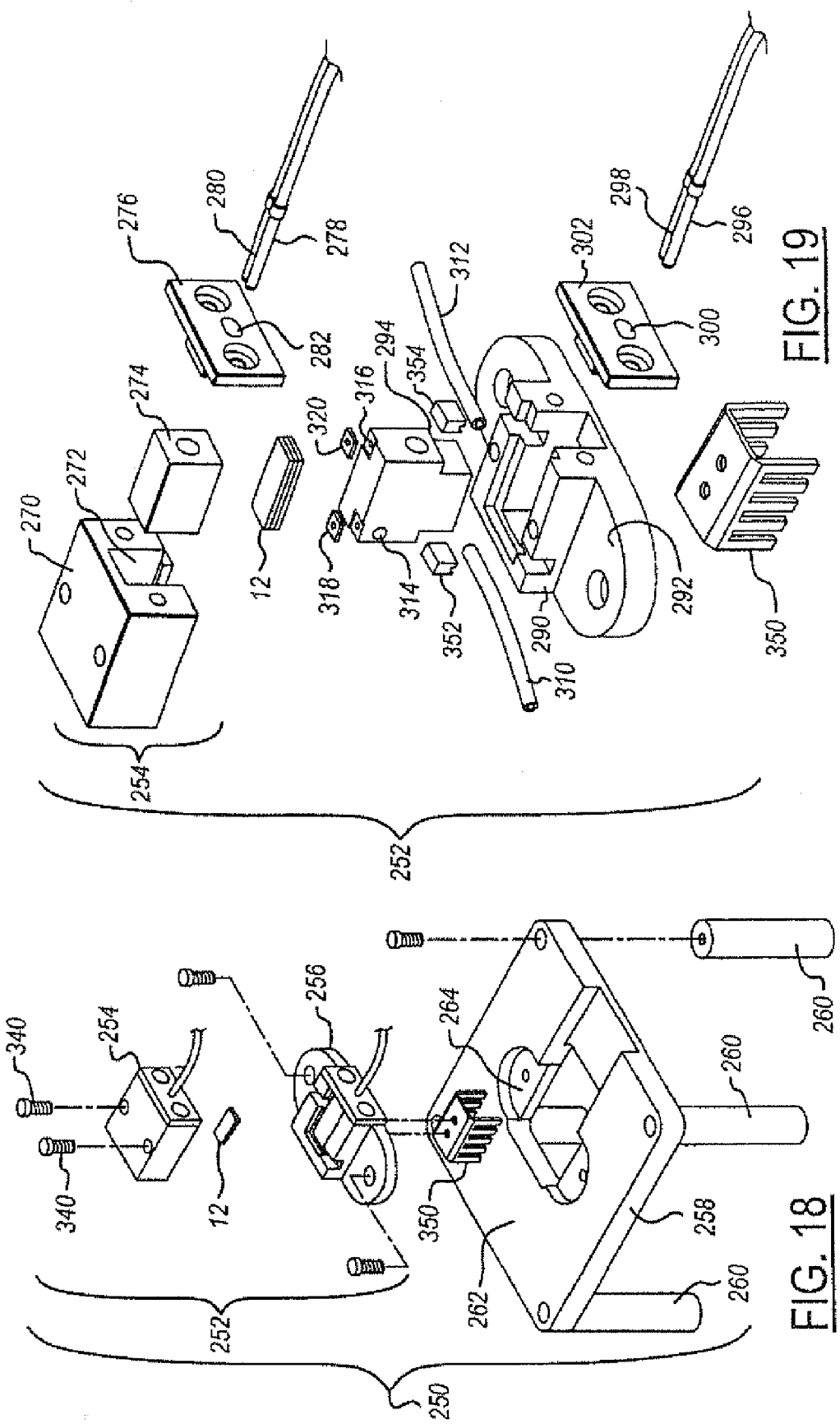

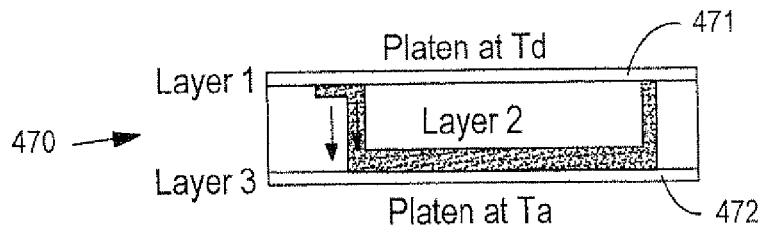
FIG. 25A
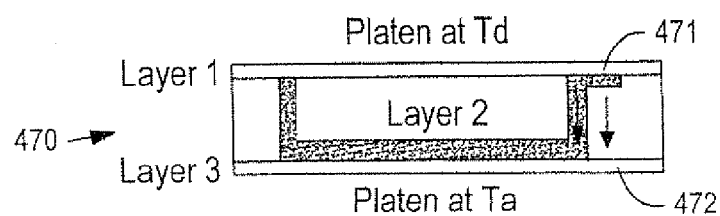
FIG. 25B
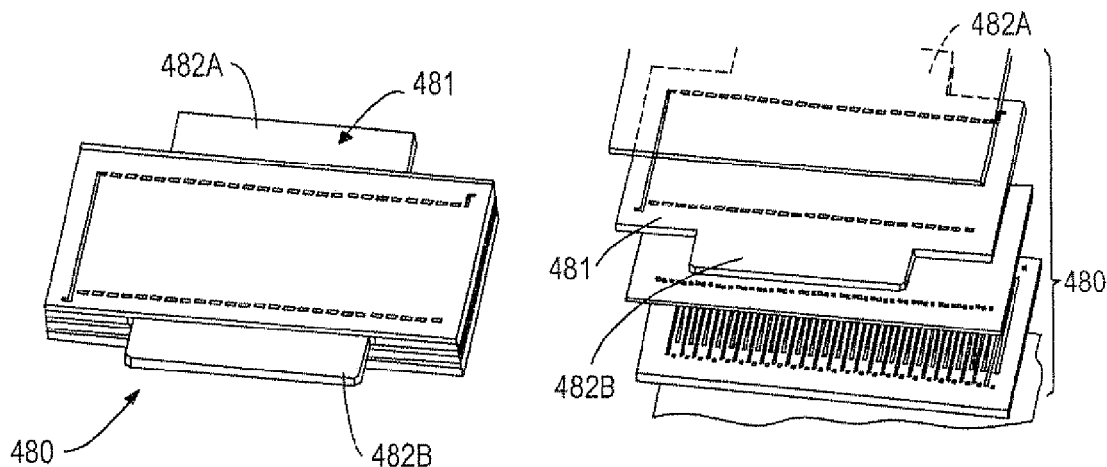
FIG. 26
FIG. 27
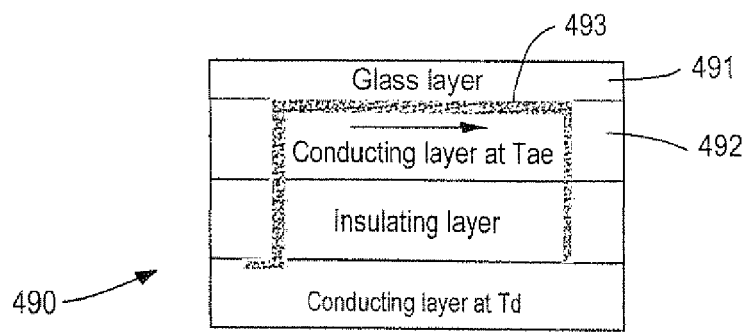
FIG. 28

THERMAL CYCLING DEVICE

RELATED APPLICATION

The present application is a continuation-in-part of U.S. patent application Ser. No. 10/906,546 now U.S. Pat. No. 7,618,811, filed on Feb. 24, 2005. The present invention also claims priority to U.S. provisional applications 60/547,036, filed Feb. 24, 2004, 60/629,910, filed Nov. 22, 2004, and 60/746,550, filed May 5, 2006, the disclosures of which are incorporated by reference herein.

TECHNICAL FIELD

The present invention relates generally to a thermal cycling devices, and more specifically, to a multi-layer thermal cycling devices suitable for the life science, medical devices and biotechnology fields. One suitable application is to perform a polymerase chain reaction (PCR).

BACKGROUND

Various fields such as life science, medical devices and biotechnology often require thermal cycling for performing various reactions. One type of reaction is the polymerase chain reaction (PCR) in which a biological sample such as a DNA fragment is replicated.

PCR has been the preferred method for replicating, or "amplifying" specific and singular nucleic acid constituents in an otherwise complex sample. Among the requirements of the PCR protocol is that the PCR sample, consisting of the biologic sample and PCR reagents, be exposed to three distinct temperatures for a specific length of time. The temperature and time of the exposure is optimized for the particular nucleic acid sequence desired. It is also a requirement that the PCR sample be exposed to the three temperatures multiple times. In the scientific vernacular, these two requirements are commonly referred to as thermal cycling.

Scientific endeavors such as the Human Genome Project and other similar efforts require that an extraordinary number of PCR reactions be conducted. The costs and time associated with the performance of PCR can become prohibitive for scientific studies that require thousands or even millions of PCR reactions. Cost reduction can be realized by reducing the volumes of the materials required for a successful PCR reaction through miniaturization. Total PCR reaction time can be reduced by decreasing the time required for the sample to be exposed to, and equilibrate at each of the temperature set points in the prescribed PCR protocol.

Current art has relied on various means to achieve these goals. Each method and device contains one or more of the following attributes that prohibits rapid temperature changes in the PCR sample. The temperature of one or more sources of thermal energy must be changed to establish each temperature set point. The time required for this is determined by the thermal conductivity of the device material which is inherently slower than the PCR sample itself. If constant temperature thermal sources are employed, regional areas of the device equilibrate at the desired temperature set points but gradual temperature changes are established in the surrounding areas within the device due to the thermal conductivity properties of the materials. This results in a slow thermal transition of the sample as it moves through the device. The time to traverse these transition temperature ranges serves to increase the total reaction time in comparison to methods that offer abrupt or instantaneous changes. It also requires that the device be larger and therefore does not provide the highest degree of miniaturization. Thus, the full cost benefit from reduced PCR sample volumes is not realized.

There is substantial development of devices and methods to facilitate the temperature cycling, also referred to as thermal cycling. U.S. Pat. No. 6,337,435 TEMPERATURE CONTROL FOR MULTI-VESSEL REACTION APPARATUS by Daniel Chu, et al. describes an approach whereby a sample or samples in a multi-well container are subjected to temperature changes caused by physical contact between the multi-well container and a heating device. The time required to perform the thermal cycling is largely determined by thermal mass and other physical properties of the heating device and is therefore relatively slow.

The multi-well device is usually opened at the top to provide access to the wells for the introduction and removal of the sample. This creates an environment for the undesirable evaporation of the sample. The aforementioned patent, as well as others, strive to reduce this effect by implementing covers. The covers reduce evaporation but present an opportunity for undesirable condensation. This effect is often mitigated by heating the cover but this then introduces a competing temperature source to the system, further increasing the total PCR reaction time.

There has been a significant effort within the biotechnology community to create closed miniaturized devices in order to mitigate the disadvantages of the open well/vessel systems. The advantages of a closed miniaturized system would be to reduce sample evaporation, reduce condensation, and to reduce costs by using smaller sample and reagent volumes. Exemplary of such miniaturized systems is U.S. Pat. No. 6,284,525 MINIATURE REACTION CHAMBER AND DEVICES INCORPORATING SAME by Richard Mathies and Adam Woolley and U.S. Pat. No. 6,261,431 PROCESS FOR MICROFABRICATION OF AN INTEGRATED PCR-CE DEVICE AND PRODUCTS PRODUCED BY THE SAME by Richard Mathies, Peter Simpson, and Stephen Williams. Such devices are fabricated containing closed reaction chambers. Sample and reagent liquids flow into and out of these chambers through a network of fluid channels. Heating elements such as resistive wire elements are fabricated within these chambers and provide the heating energy required to execute the PCR assay.

As with the larger and open system, the thermal properties of the device and the structural design primarily determine the reaction time. Although these systems are an improvement over the previously described approach, the thermal characteristics of such a structure is a limiting factor. Also, fabricating, controlling, and monitoring of the in situ heating elements is complicated and adds appreciably to the cost of the device.

Another method that attempts to accelerate the PCR process is described in U.S. Pat. No. 6,180,372 METHOD AND DEVICES FOR EXTREMELY FAST DNA REPLICATION BY POLYMERASE CHAIN REACTIONS (PCR) by Jochen Fanzen. In this embodiment, a two dimensional network of microfluidic channels is contained within two temperature heating/cooling elements. The microchannel device is exposed to rapid temperature changes by changes in the heating/cooling elements above and below the device. This system is very efficient in the energy transfer between the heating/cooling elements due to complete physical contact with the elements. However, the total PCR reaction time is still limited by the ability to change temperature within the heating/elements and within the microchannel material.

The above-mentioned devices and methods address the issue of thermal cycling for PCR by various configurations of heating elements in an attempt optimize the energy transfer from the elements to the device and eventually the PCR sample contained there in. All of these methods and devices are limited by their ability to transfer thermal energy through the device and into the sample. Further limitations are present when the heating elements themselves must also change temperature in order to expose the PCR sample to each desired temperature set point in the PCR protocol.

It is therefore desirable to provide a thermal cycling device that reduces the thermal limitations of prior known devices as well as reducing evaporation, condensation and cost so that a device for rapidly performing thermal cycling is provided.

SUMMARY

The present invention provides a method and apparatus for improved thermal cycling performance.

In one aspect of the invention, an apparatus includes a first layer, a second layer proximate to the first layer, a third layer proximate to the second layer opposite the first layer, and a continuous channel. The continuous channel is formed within the first layer, second layer and third layer. The continuous channel has a plurality of cycle segments. Each of the cycle segments comprises a first portion disposed within the first layer, a second portion disposed within the second layer, and a third portion disposed within the third layer.

In a further aspect of the invention, a device for performing a reaction comprises a first heating means, a first thermally conductive layer thermally coupled to the first heating means, a first insulating layer proximate the first thermally conductive layer, a second thermally conductive layer directly adjacent to the first insulating layer and a second insulating layer directly adjacent to the second thermally conductive layer. A third thermally conductive layer is disposed proximate to the second layer opposite the first layer. A continuous channel is formed through the first thermally conductive layer, the first insulating layer, the second thermally conductive layer, the second insulating layer, and the third thermally conductive layer. The continuous channel has a plurality of cycle segments, each of the cycle segments comprising a first portion disposed within the first thermally conductive layer, a second portion disposed within the third thermally conductive layer, and a third portion disposed within the second thermally conductive layer.

Additional embodiments of the invention include two and three layer devices which include the fluid channels in one or more of the insulating layers. Other embodiments include fluid flow channels which "fold back" from one-side of the device to the other in the same layer or temperature strata. Further embodiments include tabbed connectors to one or more of the thermal conductive layers in order for heating or heat sinking purposes.

In yet another aspect of the invention, a method of performing a reaction comprises introducing a sample into a device having a first layer, a second layer, and a third layer performing a first portion of a cycle in a first layer at a first temperature, moving the sample to the third layer, thereafter performing a second portion of the cycle in the third layer at a second temperature lower than the first temperature, moving the sample to the second layer, thereafter performing a third portion of a cycle in the second layer at a third temperature between the first temperature and the second temperature, and repeatedly performing the first portion, second portion and third portion for a predetermined number of cycles to perform the reaction.

Other method embodiments include two and three layer devices which move the samples through channels in one or more of the insulating layers and other devices wherein the channels "fold back" from one side of the device to the other in the same layer or temperature strata.

One advantage of the invention is that only two sources of thermal energy are required to perform a polymerase chain reaction that uses three different temperatures. Advantageously, because the upper and lower layers are maintained at a temperature, delays due to thermal cycling of the individual layers are not present. This accelerates the entire process compared to the existing art.

Other advantages and features of the present invention will become apparent when viewed in light of the detailed description of the preferred embodiment when taken in conjunction with the attached drawings and appended claims.

BRIEF DESCRIPTION OF THE DRAWINGS

Various features and advantages of the present invention will become readily apparent upon reading the following detailed description upon reference to the attached drawings, in which:

FIG. 18 is a perspective view of a fluidic test device formed according to the present invention.

FIG. 19 is an exploded view of the device of FIG. 18.

FIGS. 25A and 25B illustrate another two-temperature device in accordance with the present invention.

FIG. 26 illustrates a thermal cycling device with tabbed connectors in the conducting denaturation layer.

FIG. 27 is an exploded view of the thermal cycling device of FIG. 26.

FIG. 28 schematically illustrates still another thermal cycling device in accordance with the present invention.

DETAILED DESCRIPTION OF THE PREFERRED EMBODIMENT

Figure 1:
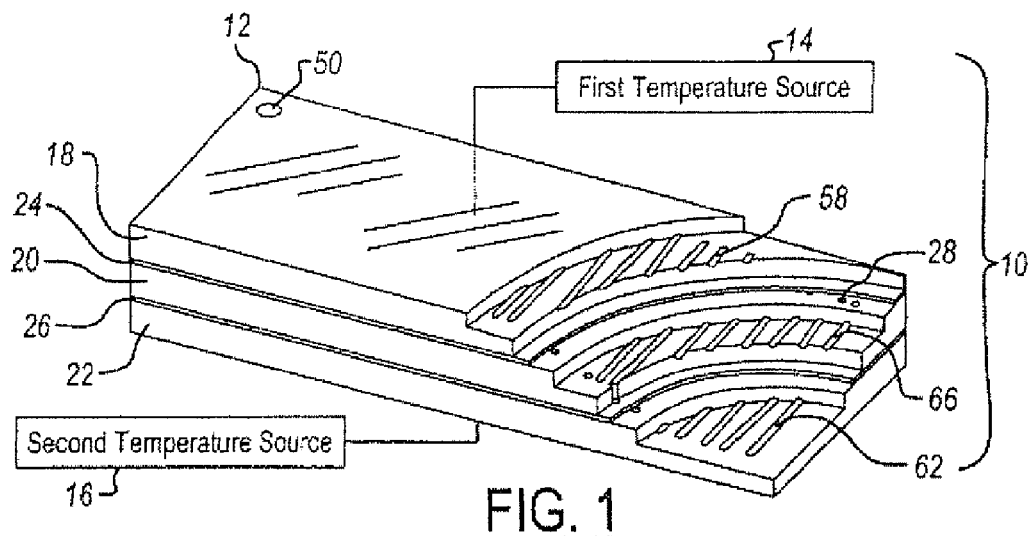
FIG. 1 is a perspective view of first embodiment of the thermal cycling device according to one embodiment of the present invention.

In the following figures the same reference numerals will be used to identify the same components. It should be noted that various examples including reagents, time, materials, and channel configurations are set forth below by way of example and are not meant to be limiting. The present invention is also described with respect to a polymerase chain reaction (PCR). However, various biological and chemical fields may benefit by the use of the present invention. It should also be noted that although the device is suitable for thermal cycling, a heating device may not be integral to the apparatus. That is, the heating device may be an external device coupled to the apparatus.

Referring now to FIG. 1, a thermal cycling device 10 includes a fluidic device 12, a first temperature source 14, and a second temperature source 16. The fluidic device, as illustrated, is formed of a first thermally conductive layer 18, a second thermally conductive layer 20, and a third thermally conductive layer 22. The layers may be planar and rectangular in shape. The layers may also be separate layers or strata of the same thermally conductive layer. That is, in a device the layers may be areas where the temperature is the same across the device. The materials of the device may be the same or different, with or without insulation as will be further described below. Various types of materials having high thermal conductivity may be used for the present invention. The high thermal conductivity causes the temperature across the layer to become isothermal. For example, metals such as steel on aluminum and semiconductors such as silicon are most preferred materials. However, other materials such as glass and various types of composite plastics may be used for the thermally conductive material. Each layer may be formed of a different or the same materials. The layers are proximate to each other. That is, the layers may be directly adjacent, adjacent, or have heaters, insulators or other structures disposed therebetween.

Figure 2:
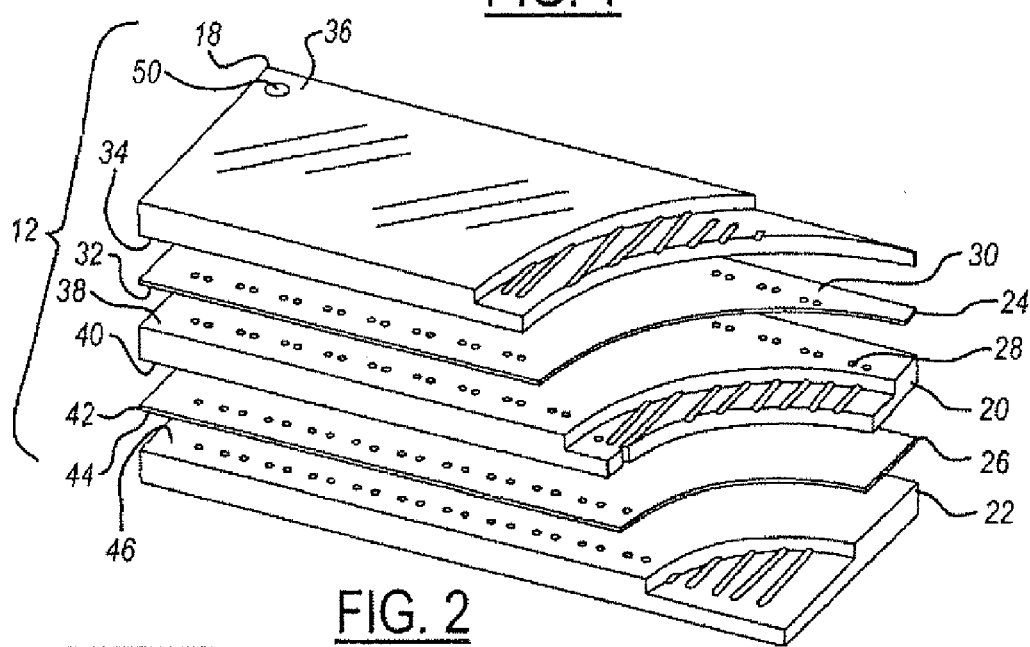
FIG. 2 is an exploded view of the thermal cycling device of FIG. 1.

Insulating layers may be used to at least partially thermally isolate the various layers. A first insulator 24 is disposed between the first thermally conductive layer 18 and the second thermally conductive layer 20. A second insulator 26 is disposed between the second thermally conductive layer 20 and the third thermally conductive layer 22. The first insulator 24 and second insulator 26 may be formed as a planar layer between the thermally conductive layers. Of course, other embodiments of such an insulator would be evident to those skilled in the art. The first insulator 24 and second insulator 26 are preferably fabricated from materials with low thermal conductive properties, such as polypropylene, polycarbonate, polyethylene or polyimide. As is best shown in FIG. 2, the insulators 24, 26 include various ports 28 therethrough so that fluid may be transferred between the thermally conductive layers. These layers may be drilled or deep reactive ion etched. The insulators 24, 26 act as a thermal buffer between the layers so that three temperatures may be maintained using two temperature sources. That is, each of the layers rapidly equilibrate and thus are isothermal. By providing isothermal layers the temperature transfer is extremely rapid. The two limiting factors in a PCR process will be the thermal absorption of the sample and the enzymatics of the chemistry. Thus, PCR may be performed as fast as nature will allow.

Ports 28 may be formed in various manners including drilling or laser ablation. When in a layer form, the first insulator has a top surface 30 and a bottom surface 32. The top surface 30 is adjacent to the bottom surface 34 of the first conductive layer 18. The bottom surface 32 of the insulator 24 is directly adjacent to the top surface 38 of thermally conductive layer 20. The bottom surface 40 of second thermally conductive layer 20 is directly adjacent to the top surface 42 of the second insulating layer 26. The bottom surface 44 of insulator 26 is directly adjacent to the top surface 46 of third thermally conductive layer 22. The top surface 36 of first thermally conductive layer 18 has an inlet port 50 therein. Inlet port 50 may be used to provide a fluid sample to the fluidic device 12. An outlet port 52 is used to remove the fluid sample from the fluidic device 12. The layers may be coupled together using a thin layer of epoxy or other adhesive. Alignment guides or pins may be used in alignment of the device during manufacturing.

Figure 3:
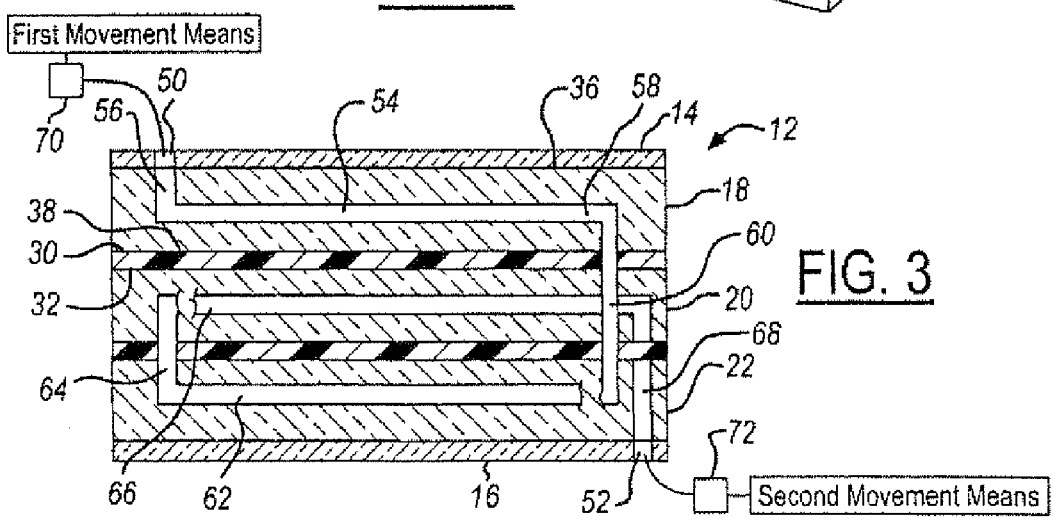
FIG. 3 is a partially broken away cross-sectional of the thermal cycling device illustrated in FIGS. 1 and 2.

As will be further described below, various types and positions of temperature sources 14, 16 may be used. Separate devices such as platens or integral devices may be used. As is illustrated in FIG. 3, the first temperature source 14 and the second temperature source 16 are directly adjacent to the top surface 36 of the thermally conductive layer 18 and the bottom surface 48 of third layer 22, respectively. The layered temperature sources 14, 16 are thus integral to the device 12 in FIG. 3.

An outlet port 52 is illustrated through third thermally conductive layer 22. The outlet port allows the fluid sample to exit the device. A continuous channel 54 is illustrated through the device. The continuous channel may be broken into various cycles that have portions corresponding to each layer of the device. In a PCR environment, three different temperatures are desired. Exposure to three different temperatures forms one amplification cycle of the PCR reaction.

The continuous channel includes an entry portion 56, a first cycle portion 58 disposed within the first thermally conductive layer 18, and a connection portion 60 that couples the fluid sample from the first thermally conductive layer 18 to the third thermally conductive layer 22. The third thermally conductive layer 22 has a second cycle portion 62 therein and is thus exposed to a second temperature less than the first temperature of the first thermally conductive layer. The second cycle portion 62 is fluidically coupled to a second connection portion 64 that couples the fluid from the second cycle portion 62 to the third cycle portion 66. The third cycle portion 66 is disposed within the second thermally conductive layer 20. As will be described below, various numbers of cycles through the first portion 58, second portion 62, and third portion 66 may be performed depending on the various parameters and desired amplification in a PCR process. Once the predetermined number of cycles through the device is performed, the fluid sample leaves the device through the third layer 22 through an exit portion 68. Exit portion 68 is performed when the fluid passes through the desired number of cycles formed in the fluidic device 12. The lengths and cross-sectional areas of the first portion 58, second portion 62, and third portion 66 are sized so that the fluid sample in each pathway is exposed to the temperature for a predetermined amount of time. The size of the pathway may be changed by varying the cross-sectional area and the length. The dwell time is proportional to length and inversely proportional to channel cross-sectional area. The fluid inlet 50 and fluid outlet 52 may be positioned in various layers. The position may be dictated as a matter of convenience depending on the configuration of the equipment to which the fluidic device is attached.

The first temperature source 14 and second temperature source 16 may be formed of various types of materials such as electric thin film devices, resistive wire devices, platens or other sources of constant temperature. In the embodiment of FIG. 3, the temperature of the upper layer is maintained at a first temperature with the first temperature source 14 and the third layer 22 is maintained at a second temperature less than the first temperature by the second temperature source 16. The upper surface of the first layer and the lower surface of the third layer 22 are illustrated as being contacted by the temperature sources 14, 16, respectively. It should be noted that the edge or edges of one or both of the layers may also be contacted by the temperature sources. Preferably, the temperature sources are regulated. Various feedback devices such as thermistors or thermocouples may be used to provide feedback to a controller. The second thermally conductive layer 20 absorbs heat from each of the layers in a controlled manner through the insulators 24, 26. That is, the amount of absorption may be controlled by controlling the amount of thermal transfer through the insulating layers by thickness or material choice. The temperature of the second layer is maintained at a third predetermined temperature between the first temperature and the second temperature. It may take a finite amount of time for the entire device to reach equilibrium. The conductive layers are preferably highly thermally conductive and thus are isothermal. After an equilibrium is reached, fluid or fluid samples may be passed through and may be exposed to each of the different layers in each of the different cycles through the continuous channel 54. Because the layers 18, 20 and 22 may be highly thermally conductive, low or nearly no temperature differentials may be supported within the thermally conductive layers. Because the insulating layers 24 and 26 are of low thermal conductivity materials, high temperature differentials may be supported within these layers. The second thermally conductive layer 20 or extension layer is warmed by the influx of heat from the first conductive layer 18 or denaturation layer through the upper insulating layer. The second thermally conductive layer 20 or extension layer is cooled by convection, radiation and conduction from its edges, efflux through the lower insulating layer and by the influx of liquid from the annealing layers. Its steady state temperature is the result of balancing these competing energy fluxes. Edge losses can be made negligible by the design of a holder for the device. The thermal resistance of the insulating layers is selected with two considerations. When no liquid is flowing, the steady state temperature of the extension layer will be set by the relative thermal resistance of the two insulating layers. When flow is present, the steady state temperature of the extension layer will drop by an amount that depends on how much energy is required to heat the influx of liquid. This drop must be within the range of extension temperature that PCR can allow. The constraint sets an upper bound on the thermal resistance of the insulating layer and, therefore, a lower bound on the energy that must be supplied to the device. In general, the energy that must be supplied to the device consists of two terms, both proportional to the difference between the denaturation and annealing temperatures. The first term is the part that establishes the steady state heat flux in the absence of liquid and second term is due to the overhead of heating liquid entering the denaturation and extension layers. Ignoring edge effects, all of the energy supplied to the device may be removed with suitable heat sinking.

The fluid sample has a rate of absorption which is one limiting factor to the speed of the process. The enzymes of the chemistry may also limit. Contrary to the prior art, the present device is limited by only these two constraints. The geometry of other art limits the speed of those processes. Typically, long pathways exist to achieve thermal isolation in such devices.

Once the fluid is placed within the continuous channel 54, various means for moving the sample may be provided such as capillary forces, vacuum, a pressure source or other means. The movement means is illustrated as a first movement means 70 and a second movement means 72. One or both means 70, 72 may be present.

The size, materials and fabrication techniques employed in this embodiment may be selected to most effectively address the needs of the specific application. For example, molding, machining, casting, extruding and various types of metals and plastics may be used for the fluidic device 12. Also, various types of heaters may also be employed. Micro-electrical mechanical systems (MEMS) may also be used to fabricate such a device. Photolithographic processes may result in the creation of multiple layers of dissimilar materials that contain the appropriate pathways, entry and exit ports, and ports through the device. Also, one fluidic device is illustrated. It should be noted that multiple fluidic devices may be employed adjacent to each other in a multiple reaction device. That is, several reactions may take place simultaneously or sequentially within the device. The fluid path may be several individual channels connected in parallel. This may be useful for thermal cycling large volumes of fluid more rapidly. The device may also be disposable in a one-time use application, or may be washed and reused.

Figure 4:
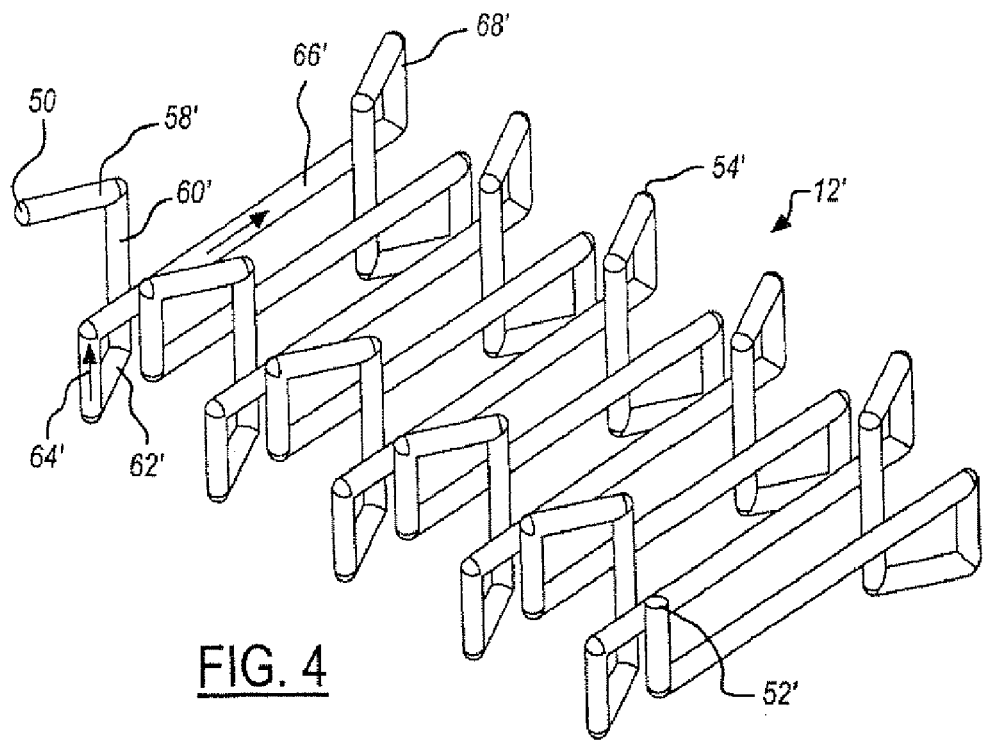
FIG. 4 is a perspective view of the channel of the device of FIGS. 1 through 3.
Figure 6D:
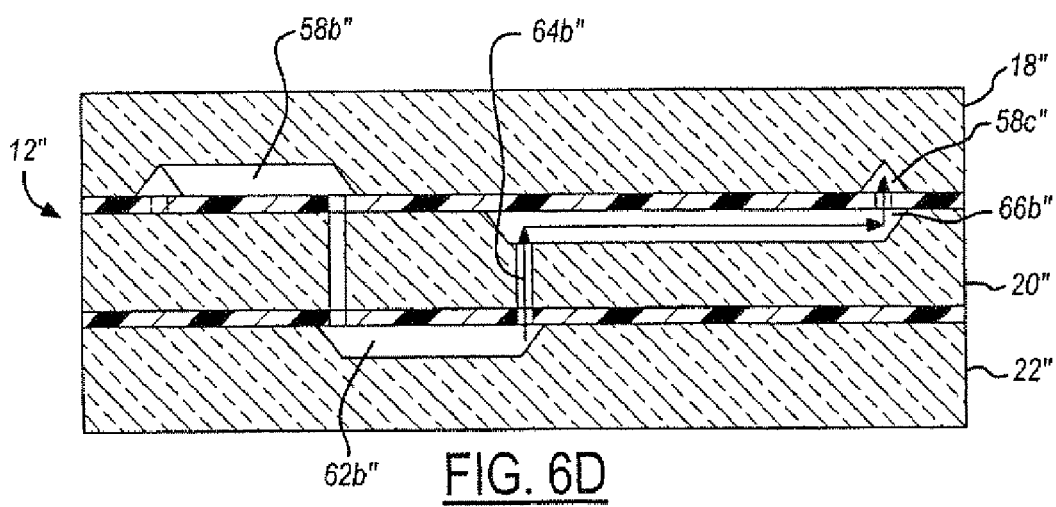
FIGS. 6A-6D are cross-sectional views of the device of FIG. 5.

Referring now to FIG. 4, a ten cycle device 12' is illustrated without the layers and only showing the continuous channel 54'. In this embodiment the first portion 58' of the continuous channel 54 is illustrated. The connection portion 60' connecting the first portion to the second portion 62' is also shown. After leaving the second portion 62' the fluid enters the second connection portion 64'. Fluid then enters the third portion 66' before entering the third connection portion 68'. Thus, the portions 58 through 68 illustrate one cycle through the device. In a PCR device the first portion is a denaturing portion. The first portion 58' is a denaturing portion. The second portion 62' is an annealing portion, and the third portion 66' performs an extension portion. In this illustration the cycle repeats ten times until the sample reaches the outlet 52' which is illustrated in an upward position and thus would correspond to the thermally conductive layer 18. Various positions of the inlet port 50 and the outlet port 52 may be evident to those skilled in the art. In this embodiment, the channels may be formed of a tubular structure and overmolded to form a unitary device. It should also be noted that the tubular device may be overmolded in the three thermally conductive layers described in FIGS. 1-3.

Figure 5:
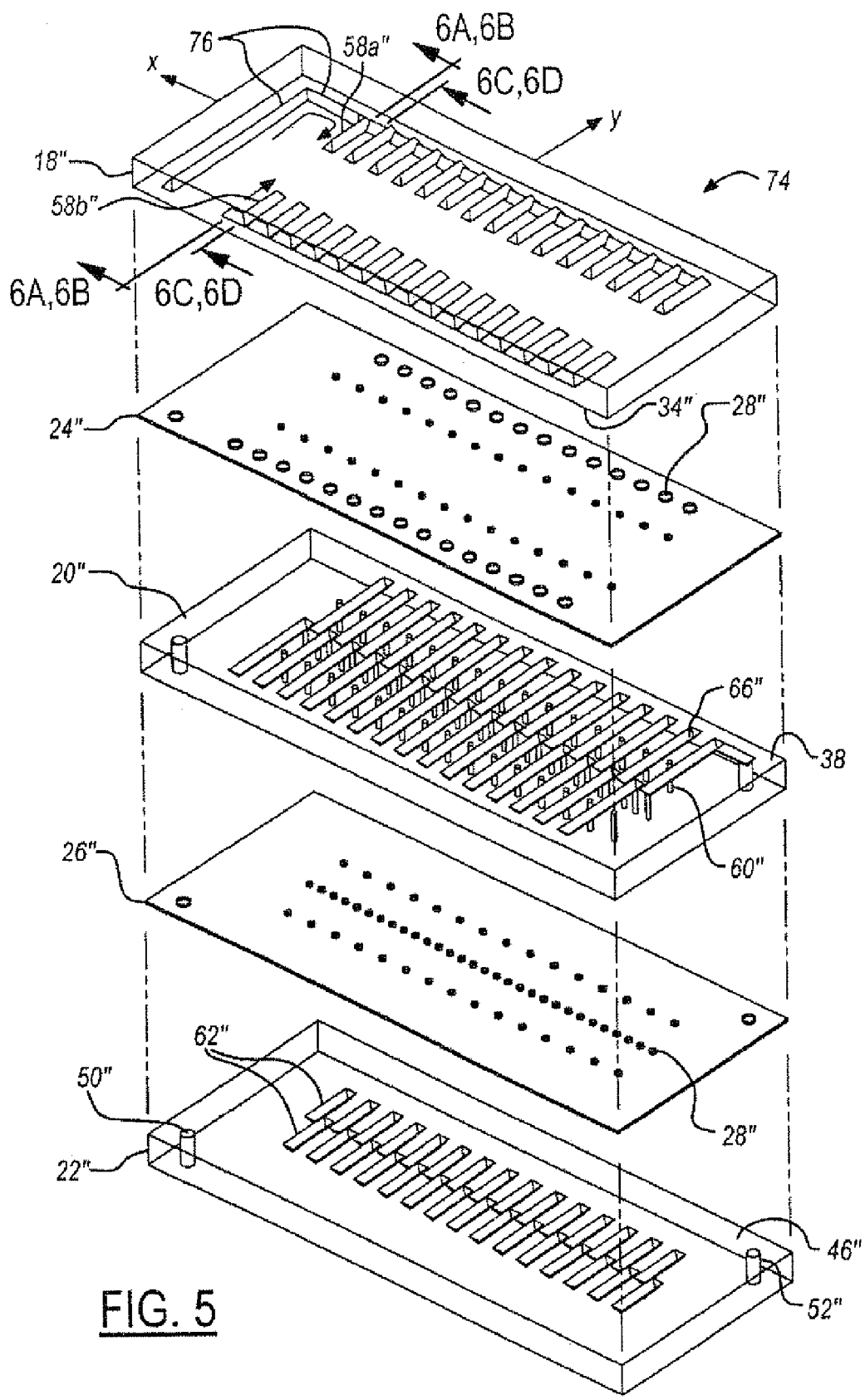
FIG. 5 is an exploded view of a second embodiment of the invention.

Referring now to FIG. 5, an exploded view of a second embodiment 74 is illustrated. In this embodiment the fluid inlet port 50" is disposed in the third layer 22". The fluid inlet port 50" extends through the second insulator 26", the second thermally conductive layer 20", the first insulator 24", and the first thermally conductive layer 18". An initial denaturing channel 76 is formed within the thermally conductive layer 18". In this constructed embodiment, the initial denaturing channel 76 was 6.5 mm. The channel portions set forth in this embodiment are triangular in cross-section. The channels were formed using orientation dependent etching using photolithographic techniques. A plurality of first cycle portions 58" are illustrated within the first thermally conductive layer 18". The first cycle portions 58" is fluidically coupled to the initial denaturing channel 76. In this embodiment a plurality of connection portions 60" are illustrated. These portions may be drilled or deep reactive ion etched. This embodiment has a longitudinal axis X and a lateral axis Y. Each of the first portions 58", second portions 62", and third portions 66" are laterally disposed except for a slight L-shaped variation on the first portion 58". In this embodiment, fluid flows generally from the thermally conductive layer 18" to the third layer 22" through the first connection portion 60". Fluid then enters the extension plate which is the second layer 20". Fluid thus passes laterally outwardly from the center of the third portion 66" where it then passes up to one of the rows of first portions 58". As will be illustrated below in FIG. 6, the fluid passes through alternate sides of the device for each cycle. In this embodiment the channels are etched in the lower surface 34" of the first thermally conductive layer 18", in the top surface 38" of the second layer 20", and in the top surface 46" of the bottom layer 22". The first insulator 24" and the second insulator 26" help define the fluid passage channels. In the constructed embodiment, 30 PCR cycles are performed with a 6.5 mm initial denaturing channel, wherein the next and subsequent denaturing channels are 1 mm long. The annealing channels or third portions 66" are also 1 mm long. The extension channels or the second portions 62" are 2 mm in length. It should be noted that an epoxy or other adhesive may be used to couple the conductive and insulative layers together.

The device may be fabricated using techniques borrowed from thermal ink jet cartridges and integrated chip manufacturing. The device may be formed of silicon and later diced after being bonded together. Alignment features may be incorporated into the device to allow various fixtures to assist in assembling the device.

Figure 6A:
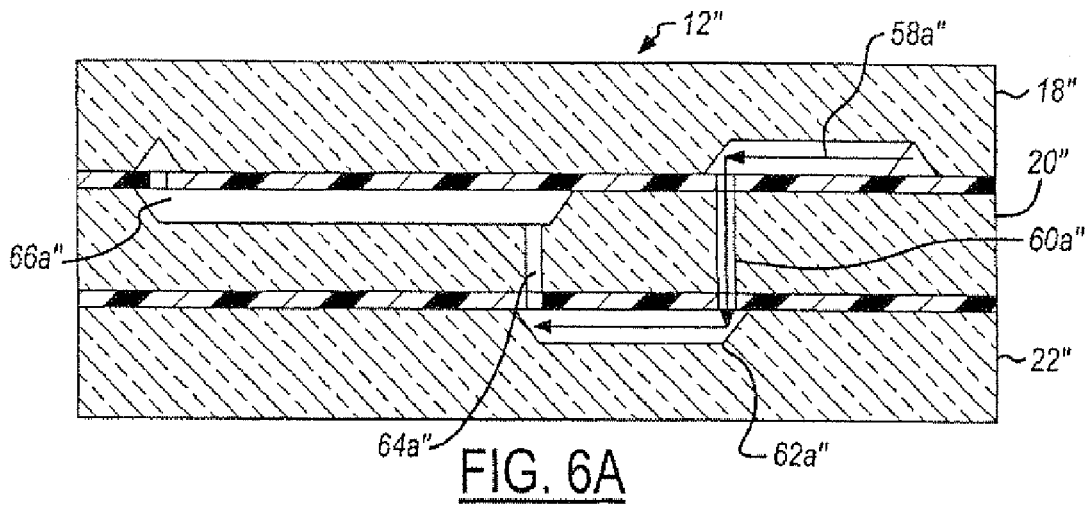
Figure 6B:
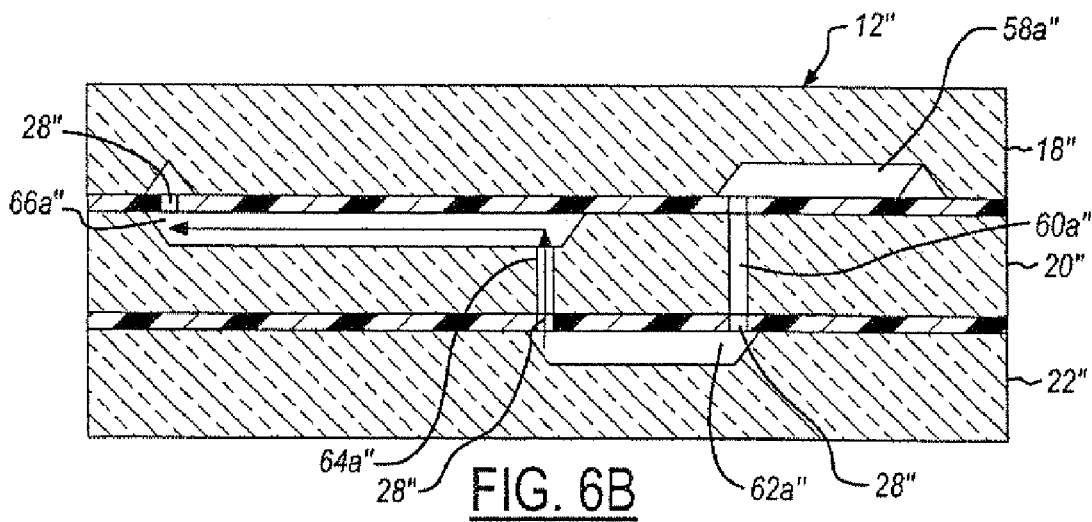
Figure 6C:
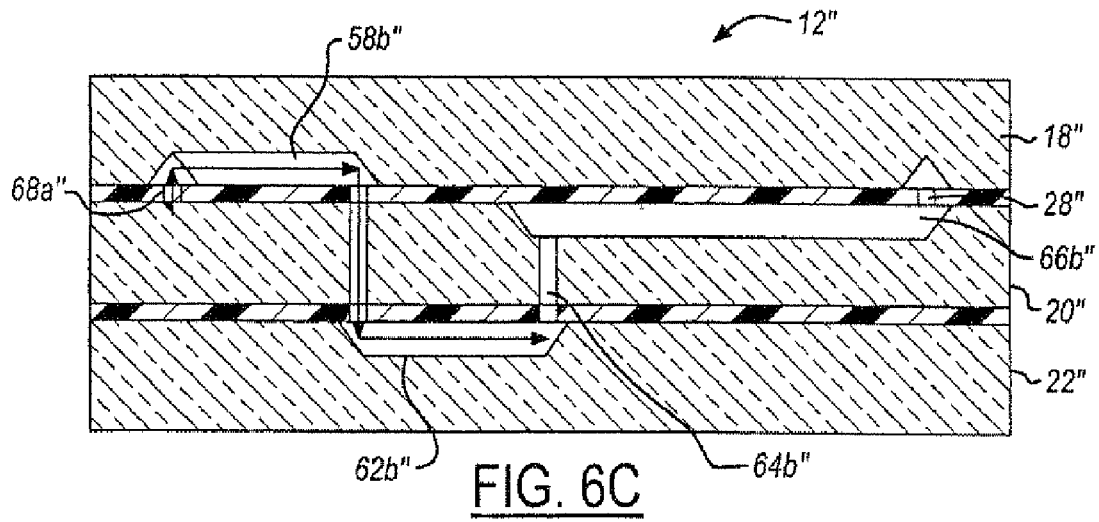

As is best illustrated in FIGS. 6A-6C, fluid flow in a first cycle portion 58a" extends laterally inwardly and through the first connection portion 60a" where it enters second cycle portion 62a". The fluid flow within the second cycle portion 62a" is also laterally inwardly. Fluid then flows through one of the second connection portions 64a" laterally outwardly through a third cycle portion 66a". Thus, the fluid at this point is on a laterally opposite side of the fluidic device 12" than when the fluid entered within the first cycle portion 58a". The fluid then enters a third connection portion 68a" where it enters another first portion 58b" on the opposite side of the device from the first cycle portion and travels laterally inwardly in a direction opposite to that from the first cycle. When the fluid enters the first portion 58b", a second cycle is initiated. Fluid then flows in an opposite direction to those described above in that within the second portion 62b" the fluid flows laterally inwardly from the left side to the middle of the device. When transitioning between the various thermally conductive layers the fluid passes through various ports 28" in each of the first insulator 24" and second insulator 26". Also, in this embodiment the outlet port 52" is through the third thermally conductive layer 22". As is best show in FIG. 3, the third cycle begins in the first cycle portion 58c".

Figure 7:
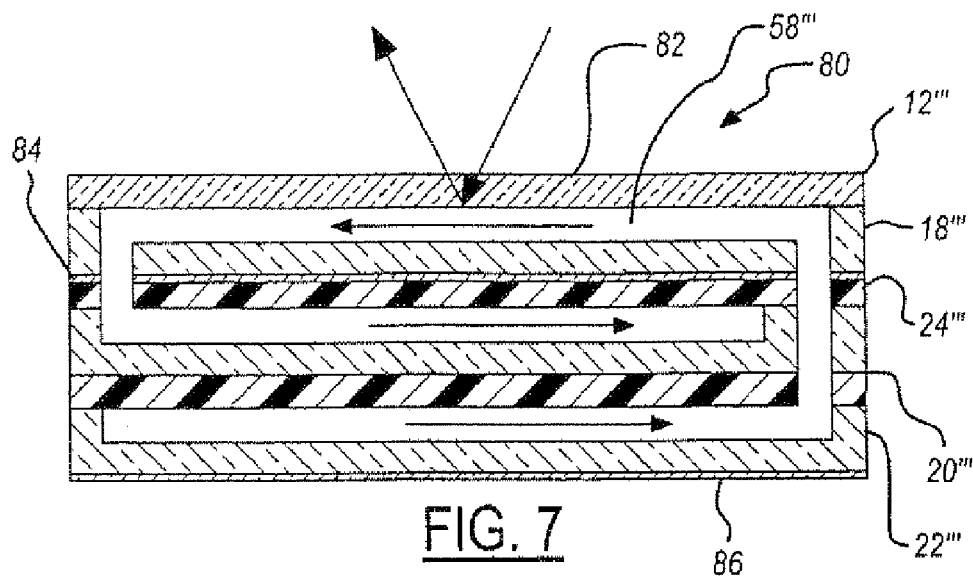
FIG. 7 is a cross-sectional view of a third embodiment of a thermal cycling device of the present invention.

Referring now to FIG. 7, a third embodiment 80 of fluidic device 12'" is illustrated. In this embodiment, a glass layer 82 is provided upon the first thermally conductive layer 18'". The glass layer 82 allows fluorescent or other optical detection therethrough. The glass layer 82 is preferably transparent at the detection wavelength and thus the amount of DNA within the first portions 58'" may be monitored. Also, in this embodiment a heater layer 84 is employed between the first thermally conductive layer 18'" and the first insulator 24'". A second polysilicon heater layer 86 may also be used in place of the heater illustrated in FIGS. 1-4. One suitable type of heater is a polysilicon heater. Various polysilicon coatings are commonly used for inkjet devices. Although the heater is illustrated as a separate layer doping may be used to form the layer. Also, the layer may be formed epitaxially. As is described elsewhere the heaters may contact the edges, or faces of the layers.

Figure 8:
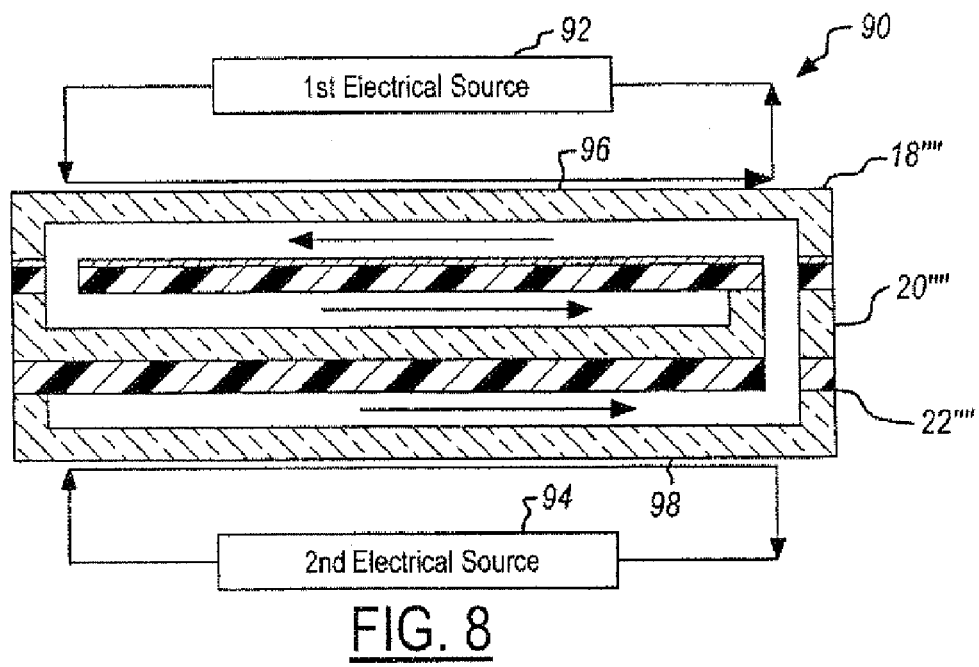
FIG. 8 is a cross-sectional view of the fourth embodiment of the thermal cycling device according to the present invention.

Referring now to FIG. 8, a fourth embodiment 90 is illustrated using an electrical "joule" heating device. A first electrical source 92 and a second electrical source 94 are coupled to an joule heater 96 and 98, respectively. That is, the joule heater 96 may be disposed on the upper surface of the thermally conductive layer 18"". The second joule heater 98 is disposed on the bottom surface of the third layer 22"". In a practical embodiment a thermocouple, thermistor or other sensing device may be required to control the temperature. The device may be external to or integrated with the thermal cycling device in various ways known to those skilled in the art.

Figure 9:
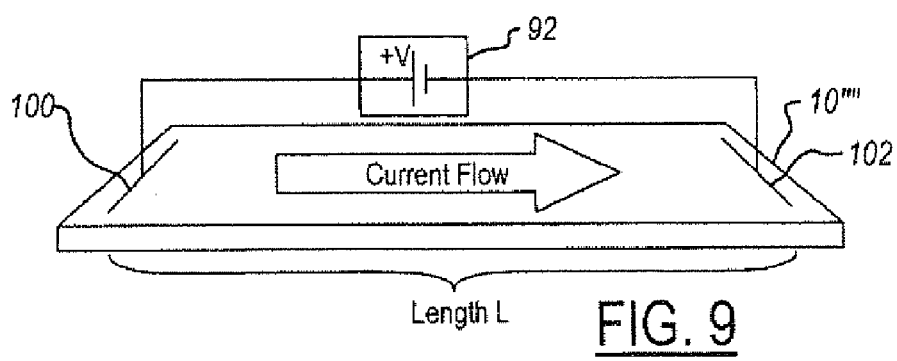
FIG. 9 is a perspective view of a heater formed according to the present invention.

As is best shown in FIG. 9, the current may pass through the device using a pair of contacts 100, 102. The electrical contact may be made on the surface or at the edges of the silicon by various commonly employed means. By providing the potential difference between the contacts 100, 102, a predetermined amount of current may pass therethrough and cause a specific amount of heating. The conductivity required may be characterized by the surface resistance of the material $q_s$ with units of ohms per square or simply ohms. $q_s$ is the bulk resistivity $q_b$ divided by the thickness of the conducting layer. In the case of bulk conduction, the entire thickness of the silicon layer may be used. In the simplest situation contact is made across the width of the device at each end as is shown in FIG. 9. Current flows through the surface layer or bulk, depending on the configuration. Power is dissipated per unit area as $V^2/q_s L^2$ and the current per unit of width is $V/q_s L$. For a device where L is 1 centimeter and $q_s$ is 10 ohms per square, applying ten volts will result in dissipation of 10 watts per square centimeter at a current density of 1 ampere per centimeter of width. Any particular device may require more but usually much less than this amount of heating.

Figure 10A:
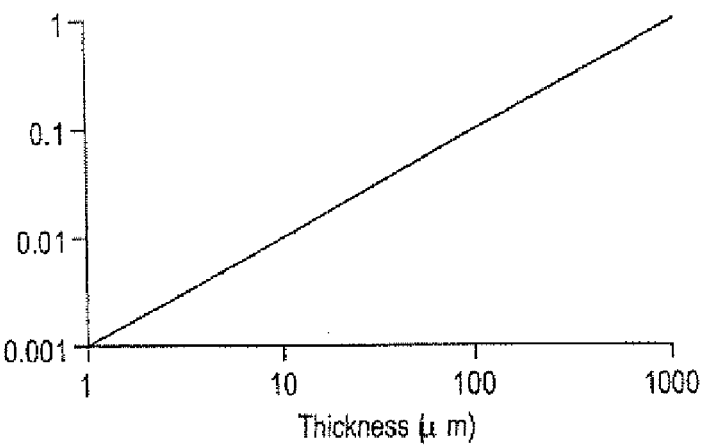
FIG. 10A is a plot of bulk resistivity versus thickness for a heater formed according to FIG. 9.
Figure 10B:
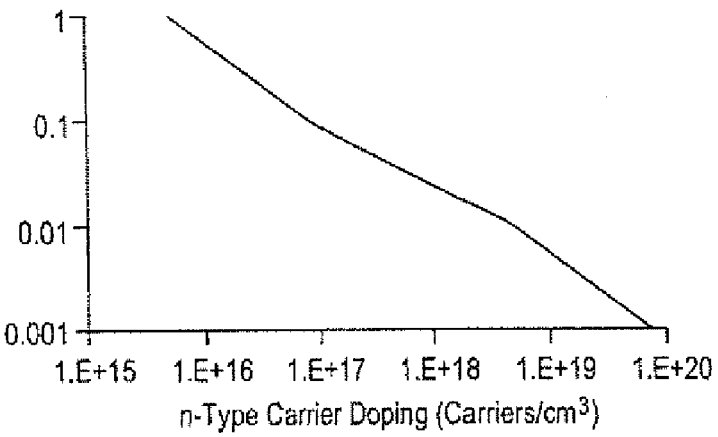
FIG. 10B is a plot of bulk resistivity versus n-type carrier doping for the heater illustrated in FIG. 9.

Referring now to FIGS. 10A and 10B, FIG. 10A shows the bulk resistivity required to achieve 10 ohms per square for a conducting layer of specified thickness. For example, a 500 micron (0.55 mm) thick silicon wafer will have a surface resistance of 10 ohms per square if the bulk resistivity is 0.5 ohms-cm. The same surface resistance will result if a 10 micron thick layer having a resistivity of 0.01 ohms-cm were created on the surface of the silicon through metal plating, ion implantation or ion diffusion techniques. If doping or implantation is to be used, FIG. 10B indicates the levels of n-type carriers needed to achieve the required bulk resistivity. P-type doping may also be used.

Figure 11:
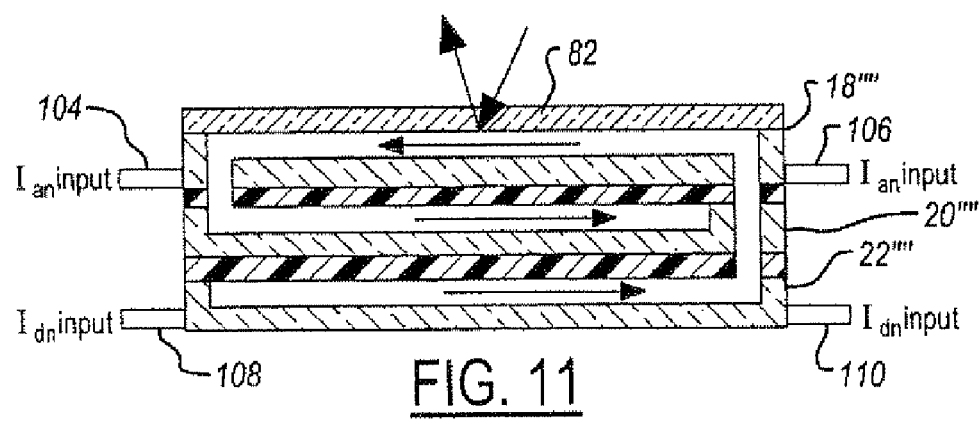
FIG. 11 is a cross-sectional view of a fifth embodiment of the present invention.

Referring now to FIG. 11, if bulk joule heating is employed in a silicon layer, contacts may be provided on the lateral (or longitudinal) edges of the device. As is illustrated, contacts 104 and 106 are provided to the first thermally conductive layer 18"". A second set of contacts 108, 110 are coupled to the third layer 22"". It should be noted that the electrical contacts may be integral to the device or separate from it. Thus, current may flow in bulk through the device and provide a specified joule heating. Such configurations may also include the glass layer 82. The various types of heaters described above may be employed with any of the embodiments described in FIG. 7, 8 or 11.

Figure 12:
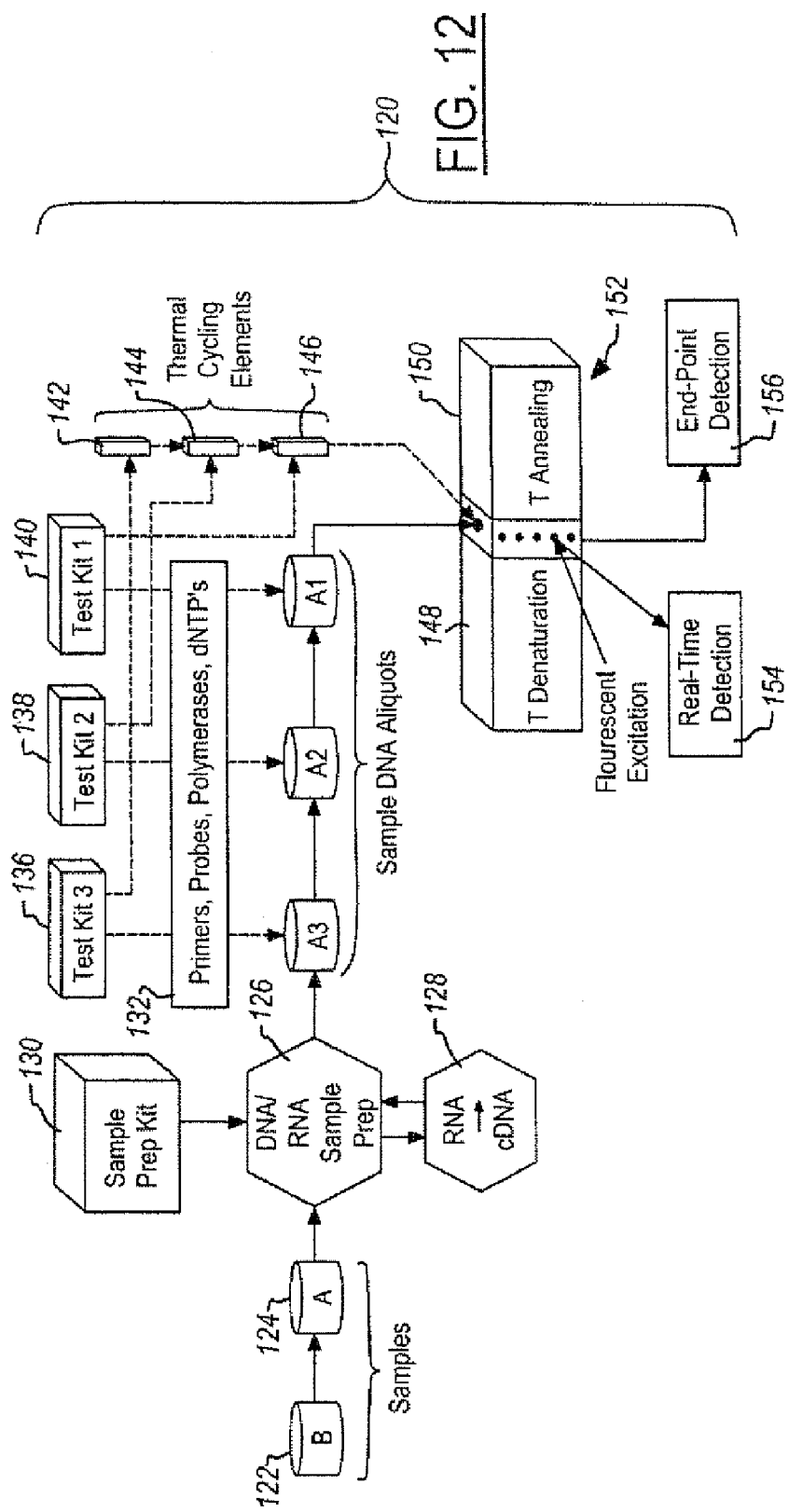
FIG. 12 is a schematic view of a PCR analyzer and kits for the same.

Referring now to FIG. 12, a random access PCR analyzer 120 is illustrated. In this embodiment, samples in sample vessels 122 and 124 are provided to the DNA/RNA sample prep block 126. A sample preparation kit 130 may be provided with the thermal cycling devices. If required, a reverse transcriptase reaction may be performed in block 128 to form cDNA from RNA. The sample preparation kit 130 is generally illustrated as block 130. The sample preparation kit 130 may be used to extract DNA material from the input sample of tissue or fluid. The sample preparation kit 130 may be integrated with the test kit. After preparation the sample aliquots are taken from the samples and dispensed into vessels A3, A2 and A1. Various primers, probes, specially buffered solutions, polymerases and dNTP's are illustrated in block 132 and may be provided within the test kits 136, 138 and 140. During the PCR process the enzymes of the process have a reaction time. The reaction time will vary depending on the particular process and the thermal absorption rate of the sample. The circulation rate of the fluid is thus limited by the absorption and the reaction time of the enzymes. Thermal cycling elements 142, 144 and 146 may also be provided within the test kits. Platens 148 and 150 may be used to provide the appropriate denaturing and annealing temperatures to the thermal cycling elements. Prior to the insertion of the samples, the thermal cycling elements are inserted between the platens 148, 150, which form an incubator 152. The thermal cycling elements 142, 144, 146 are thus brought up to the desired temperature and the samples are drawn or forced through the device at a predetermined rate. Blocks 154 provide real-time detection using fluorescent excitation, lasers or the like. At various points within the thermal cycling elements, the amount of amplification may be detected. End-point detection 156 may be provided at the end of the process. The sample may be used for various types of analysis. After the end-point detection 156, the sample and the reagent mixture may be disposed of.

The small size, expected low cost and disposable nature of the thermal cycling elements make possible the creation of a random access PCR analyzer. Prior to this embodiment, virtual all PCR reactions were performed as batch operations with the number of different reactions running simultaneously determined by the number of thermal cycling ovens in the system. One type of amplification system has two thermal cyclers and therefore can perform no more than two different protocols simultaneously. As the number of PCR tests increases over time, there will be more demand for random access analyzers. The thermal cycling device may be capable of performing a number of tests. Random access analyzers may be defined as those having the ability to run any combination of available tests on each and every sample presented to the analyzer. Thus, various numbers of heaters or built-in heaters may be provided for each thermal cycling element. Thus, various numbers of samples and various numbers of thermal cycling elements may be simultaneously performed. For example, the amount of heating may be controlled by a central controller so that various temperatures may be achieved in various thermal cycling elements. Random access analyzers have several advantages over batch analyzers. That is, they are faster, more flexible, more versatile, and more productive than batch analyzers. It is envisioned that various PCR kits may be created each containing a multiplicity of thermal cycling elements of a specific type and the necessary reagents to perform PCR amplification. The kits may include the various polymerase enzymes, dNTP's, specially formulated buffers, and primers. Optionally, other agents for sample preparation and detection may also be provided. Thus, by having the capability of programming the temperatures, various PCR test protocol may be run. The incubator 152 may include the means for drawing the fluid through the thermal cycling device. Also, various sample preparations may also be performed such as lysing cellular samples to release DNA or performing reverse transcriptase reaction to create cDNA for RT-PCR.

Figure 13:
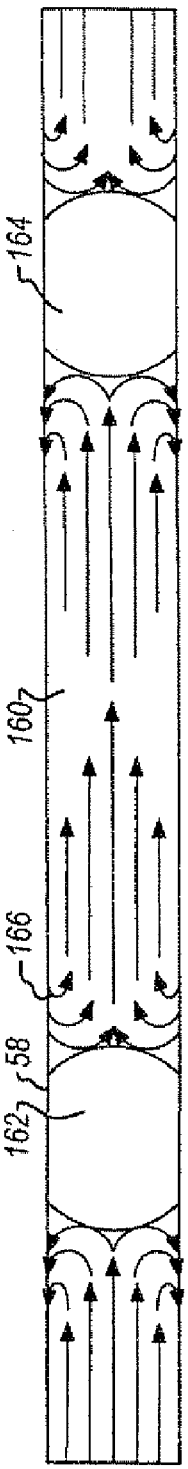
FIG. 13 is a cross-sectional view of a channel that uses bubbles to improve the thermal cycling.

Referring now to FIG. 13, a portion of the channel 54 is illustrated. This portion is illustrated as the first portion 58. A sample 160 is disposed within the first portion of the channel 58. A pair of bubbles 162, 164 delimit a sample 160 therein. The bubbles 162, 164 may be intermittently introduced into the flow with sufficient size to separate the fluid into individual sample segments 160. This is done for the purpose of promoting averaging of the temperature-time experience of the DNA solute through internal mixing (reducing the dispersion of dwell times) and segregation mixing also occurs as the fluid sample moves through a tortous path. The presence of the bubbles 162, 164 forces circulation illustrated by the arrows 166 within the fluid segment sample 160. Since the fluid at the wall must be stationary, there is a roughly toroidal flow profile. The spread in the velocity of any fluid element and consequently the spread in its time temperature profile, will be limited by the extent of the segment. Practically, it may be desirable to keep the ratio of bubbles to fluid as low as possible. In the figure, the ratio is about 20%. Since the figure also represents the overhead associated with increasing the length of the fluid column, it is desirable to keep the ratio to a minimum. A measure of the maximum dispersion of times can be obtained by comparing the length of the fluid segment to the length of a single cycle. If the fluid segment is 5-10 diameters and the length of a single cycle is 100 diameters, the dispersion times would be about 5-10%. The use of the bubbles may improve the thermal cycling because the PCR devices generally operate at low Reynolds numbers of less than 10 and often less than 1. This occurs because the amount of fluid processed is small, in the range of several nanoliters to tens of microliters. This also occurs because the heat transfer to the fluid is governed by its thermal relaxation content, which is proportional to the square of the depth and inversely proportional to the diffusivity of the fluid. The time associated therewith is a few tenths of a second when the depths are between 100 and 200 microns but may increase rapidly for channels of larger cross section due to the squared dependence. When low Reynolds numbers are associated with flow, the inertial effects are dominated by viscous forces and mixing is minimal or non-existent. In long channels flow approaches the Poiseuille flow. In the Poiseuille flow situation, there is no mixing. Material near the center flows at twice the average velocity while that near the walls creeps much more slowly. Thus, in a PCR environment the material near the center of the channel would race through the microchannels in about half the average time, potentially limiting the effectiveness of the cycle amplification. Material nearest the wall on the other hand would move much slower than the average time but other deleterious effects may be present. It should be noted that there is Brownian motion at the molecular level and thus some mixing does occur. Thus, by providing the bubbles 162, 164 described above, more thorough mixing may be provided.

Figure 14:
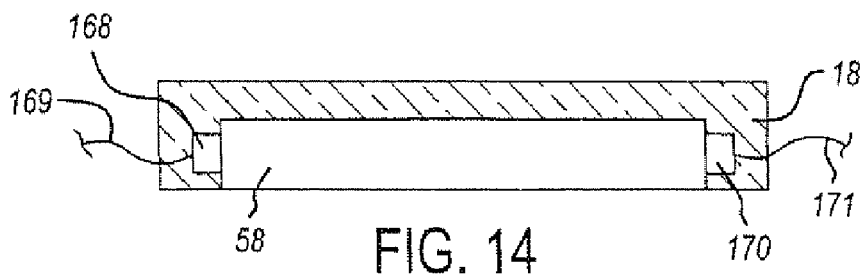
FIG. 14 is a cross-sectional view of a channel portion having an LED and a photodiode therein.

Referring now to FIG. 14, a multiplicity of LED's 168 and photodiodes 170 may be provided at various points or within various cycle portions throughout the process. As illustrated, LED's 168 and photodiodes 170 may be provided in the first portion 58. Also, the location of the photodiodes and LED's may be positioned in various locations in the continuous channels such as in each first portion, second portion or third portion or various combinations thereof. For example, all or a multiplicity of the annealing paths may include an LED and photodiode. Light filtration elements may also be used to improve the detection results. The photodiodes may thus be coupled to an analyzer device for monitoring the amount of DNA present. As mentioned above, the amount of DNA present may also be measured by fluorescence emissions through a window. A laser or LED may provide the source for fluorescence to be measured. Wires 169, 171 may be coupled to a controller or analyzer device.

External means may also be used to allow recirculation of the PCR amplification product repeatedly through the same or separate devices. Between each of the devices a detection may be performed to determine the amplification.

Figure 15:
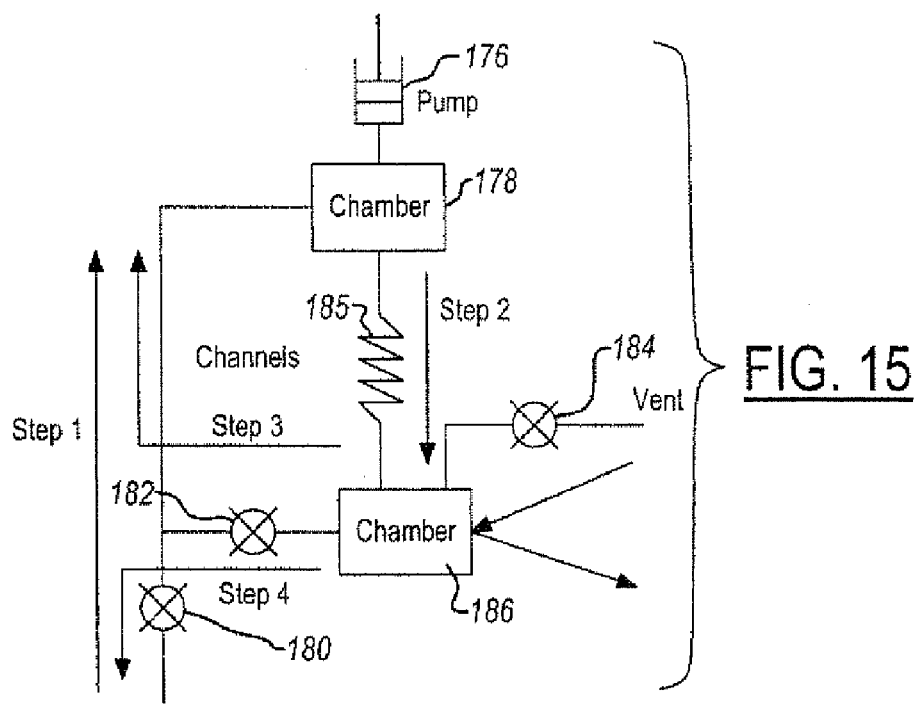
FIG. 15 is a schematic view of a device according to the present invention.

Referring now to FIG. 15, one example of a recirculating device coupled to a thermal cycling element 185 is illustrated. In FIG. 15 a pump 176 is coupled to an upper chamber 178. That is, the pump 176 draws the sample into the chamber 178. To perform this, valve 180 is opened which provides the sample to the chamber 178 when the pump is aspirated. Valves 182 and 184 are closed. Then, valve 180 is closed, valve 182 is closed, valve 184 is opened to provide venting, and the pump 176 is operated to dispense the sample into the lower chamber 186. Thus, the thermal cycling element 185 amplifies the sample as it passes from the first chamber 178 to the second chamber 186. A recycle operation may be performed by closing the first valve 180, opening the second valve 182, and opening the third valve 184 for venting. After the desired number of cycles through the thermal cycling element 185 is performed, the fluid may be dispensed by opening the first valve 180, opening the second valve 182, closing the third valve 184, and operating the pump in a dispense mode. At various times a small portion may be dispensed or an amount of amplification may be measured in the thermal cycling element 185.

As mentioned above, various techniques may be used for fabricating the device. For example, tubes may be preconfigured as set forth in FIG. 4 and then a plastic material may be molded therearound. Insulation may be molded into the various layers to separate the layers. Also, the locations of the channel layers with respect to the exterior surfaces are chosen such that the channel pathways equilibrate at three desired temperatures required by the PCR protocol.

A method for operating the present invention includes introducing a sample into the device having a plurality of layers. Prior to the introduction of a sample, the temperatures of the individual layers maintain three temperatures required in the PCR protocol. In this embodiment, the temperature of the bottom thermally conductive layer is lower than the upper thermally conductive layer. Thus, once a steady state has been reached by the three conductive layers the sample is introduced into the device. It should be noted that when thermal equilibrium, the entire upper layer is at the same temperature as the temperature source and the entire lower layer is at the temperature of the lower temperature source. Thus, the device is in equilibrium. The middle layer is at an equilibrium temperature between the upper and lower temperatures. The sample is placed through the input port and in the case of the second embodiment, is provided to an initial denaturing stage longer than the other denaturing stages. This may or may not be required depending on the type of PCR performed. The PCR sample is cycled through the first portion of a cycle at the first temperature. The sample is moved to the second layer, which is the lower layer through the third layer in between the first and second layers. The sample also passes through the insulators 24 and 26. Various means may be used to force the fluid through the fluidic device such as a vacuum, a pressure pump, a capillary force or other means. The rate of fluid flow determines the length of time the PCR sample is subjected to the highest temperature in the first portion. After the end of the first portion is performed, the fluid passes to the bottom fluidic layer through the middle layer. After traversing all three channel portions of the first cycle, the fluidic sample enters the second cycle in the first layer. As is illustrated in FIG. 5, the various rows of first portions may be provided in a compact structure so more thermal cycles may be provided in a small area.

It should be noted that various numbers of cycles may be provided in various devices depending on the type of PCR to be performed. Greater or fewer number of cycles may be provided when compared to the 30 PCR cycles of FIG. 5. As mentioned above with respect to FIG. 15, the thermal cycling element may be coupled to a device for recirculating the fluid back into the device. This may be done as a feedback response to detection stage that detects the amount of amplification. If the desired amount of amplification is not performed, the fluid sample may be recycled back into the thermal device. It should also be noted that various reagents may also be input together with the sample at various times so that a sufficient amount of reagents are available for the reaction.

Figure 16:
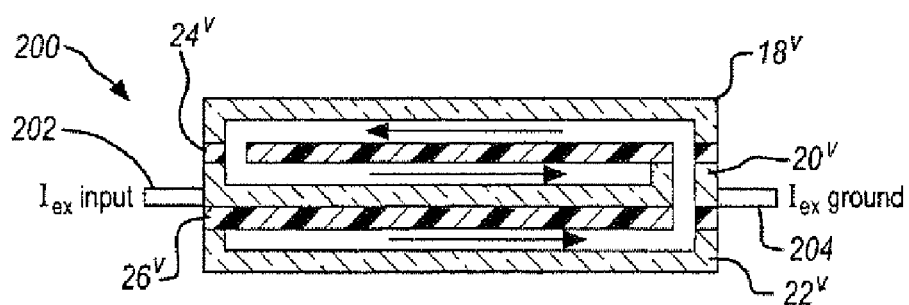
FIG. 16 is a cross-sectional view of a sixth embodiment of the invention.

Referring now to FIG. 16, a sixth embodiment of the present invention is illustrated. In this embodiment, a third temperature source 200 is illustrated. The third temperature source 200 includes a first contact 202 and a second contact 204. The contacts may be configured in a similar manner to that described above with respect to FIG. 11. That is, joule heating may be performed through the device and through the second layer $20^v$. That is, the extension layer may also be heated. In this embodiment, the insulating layers $24^v$ and $26^v$ may have increased insulating properties so that each of the layers are or are nearly thermally independent. That is, in an embodiment with three temperature sources it may be desirable to reduce or eliminate the thermal dependency of each of the layers. Of course, the heating may also be performed by an independent heating layer such as a polysilicon heater illustrated above. That is, an independent heater such as a polysilicon heater would be located between one or both of the insulating layers $24^v$, $26^v$, and the second layer $20^v$. Also, in this embodiment, various configurations for the first and second temperature sources may be included. That is, various types of heaters may be included such as a polysilicon heater, surface heating or external platens may be employed to heat the device.

Figure 17:
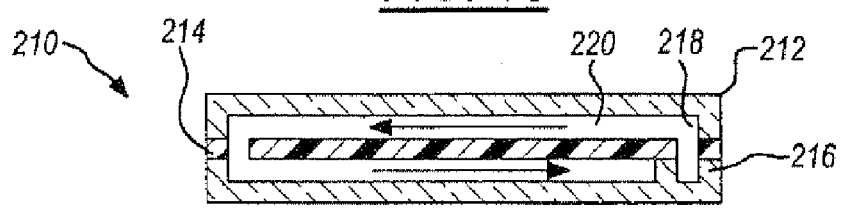
FIG. 17 is a cross-sectional view of a seventh embodiment.

Referring now to FIG. 17, a seventh embodiment 210 of the present invention is illustrated. This embodiment has only two fluidic thermally conductive layers rather than three as set forth in the previous embodiments. In this embodiment, a first layer 212 and a second layer 216 are separated by an insulating layer 214. Layers 212 and 216 are thermally conductive layers. In this example, the first layer and the second layer have continuous channel 218 therein. The continuous channel 218 has a first portion 220 and a second portion 222. The first portion 220 is disposed within the first layer and the second portion 222 is disposed within the second layer 216. In some forms of PCR, the extension temperature and the annealing temperature may overlap. Therefore, annealing and extension may be performed within the same layer. Thus, this embodiment has two layers and two different temperature portions which form the cycle. It should also be noted that the insulating layer 214 is optional. That is, the insulating layer 214 may be eliminated in some embodiments if a proper thermal gradient may be applied to a device so that the first portion and second portion have the desired temperature for the annealing and extension as well as the denaturing layer.

This embodiment also may include the various means of heating described above. That is, various platens or other types of heaters may be disposed at various portions of the device. Heaters may be disposed between the insulating layer 214 and the layer 216 or the layer 212, or both. It should also be noted that various numbers of cycles may be provided in the device.

Various embodiments with various numbers of cycles have been illustrated. It should be noted that after or during a cycle variations such as detections or additional denaturing, annealing or extension steps may be performed. For example, an extra denaturing step after the last extension step may be included. Also, elongated denaturing step may be provided at the first cycle portion or first and second cycle portions.

Referring now to FIGS. 18 and 19, a test fixture 250 for a thermal cycling device 252 is illustrated. At the center of the thermal cycling device 252 is a fluidic device 12. The thermal cycling device 252 includes the fluidic device 12 and includes an upper cap assembly 254 and a lower cap assembly 256. A fixture assembly 258 includes legs 260 coupled to a mounting top 262. The mounting top 262 includes recessed portions 264 for receiving the thermal cycling device 252. The upper cap assembly 254 and lower cap assembly 256 are a denaturing heater and an annealing heater in a PCR device.

The upper cap assembly includes a cap housing 270 having a channel 272 therein. The channel 272 receives a platen 274. An end cap 276 is used to secure the platen within the cap piece 270. A rod heater 278 and thermocouple 280 are inserted within an opening 282 in end cap 276. The rod heater is used to heat the platen to a predetermined temperature so that the temperature is imposed upon the fluidic device 12. More specifically, the upper surface of the fluidic device 12 is coupled to the platen 274.

Lower cap assembly 256 includes a lower cap housing 290 that includes a guide feature 292 to be received within the recesses 264 of top 262. A platen 294 is received within the lower cap assembly. A rod heater 296 and a thermocouple 298 are inserted within an opening 300 in an end cap 302 so that the rod heater provides heat to the lower platen 294 and thermocouple 298 is used to heat the platen to a predetermined temperature. Platen 294 may also be coupled to an input tube 310 and an output tube 312. An input channel 314 and an output channel 316 may be provided through the platen. Gaskets 318, 320 may be coupled between the fluidic device 12 and the platen 294 to prevent fluid leakage therebetween. The device is held together with threaded fasteners 340.

A heat sink 350 may be coupled to the lower cap 290. Because the upper platen 274 is at a higher temperature than the lower platen 294, heat is dissipated through the heat sink 350. This helps maintain the denaturing layers and annealing layers of the fluidic device 12 at the predetermined temperatures.

A pair of hose clamps 352, 354 may also be used to secure the input tube 310 and output tube 312 to the thermal cycling device 252.

In one constructed embodiment of the fluidic device, a cross-sectional channel area of 0.022 mm$^2$ was used. The channel length for the denaturing portions was 1 mm and the extension portions 2 mm. Thirty cycles were used in the constructed embodiment. The preliminary denaturation channel length was 9 mm. The thickness of the silicon layers was 0.575 mm. The conductivity was 130 watts/m° C. The polyimide thickness was 0.125 mm and its conductivity was 0.31 watts/m° C.

The reaction solution may include human genomic template DNA of 5 femto molar concentration. A commercial PCR buffer having critical constituents of tris-HCl buffer for pH stability and $MgCl_2$ to provide $Mg^{++}$ ions critical for polymerase activity. Deoxynucleotide triphosphates (dNTP) were provided of 200 micro molar concentrations each for A, T, C and G. Forward and reverse primers specific to the human genome template which are 20-30 nucleotides in length were chosen to define 100-200 base pair amplicons of 200 micro molar concentrations each. Taq polymerase enzyme was chosen at one unit per reaction. The test fixture described above is coupled to a syringe pump (not shown) from which the reaction solution is pumped through the thermal cycling device 12. The heated platens maintain the denaturation temperatures of 96±1° C. and annealing temperatures of 54±1° C. The platen heaters and temperature controllers having embedded thermocouples provide 16 watts each. A heat sink having a thermal resistance of 3.75° C./w were attached to the exposed surface of the annealing platen. The syringe pumps that were used have a capacity of 10 μL and flow rate of 0.22 μL/s with a 1 mm/s flow rate. The amplification product is collected at the output of the device. Various means may be used to detect the presence and the amount of amplified DNA material present in the product. Common methods employ electrophoresis to spatially separate the PCR products by molecular weight and fluorescence probes that bind to the DNA product to indicate the concentrations.

Figure 20:
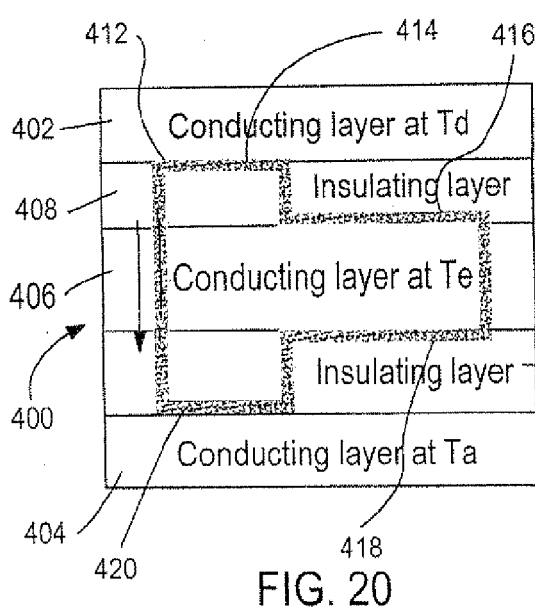
FIG. 20 schematically illustrates a three-temperature device in which fluid channels are formed in an insulating layer.

FIG. 20 schematically illustrates a three-temperature device 400 in which some of the fluid channels (i.e. "channel segments") are formed in the insulating layers. The device 400 includes a first thermal conducting (denaturation) layer 402, a second thermal conducting (annealing) layer 404, and a third thermal conducting (extension) layer 406. The three layers are separated by insulating layers 408 and 410. The cycling channel 412 includes channel segments 414, 416, 418, and 420 which reside in the insulating layers. It is preferred, but not essential, that the channel segments in the insulating layer be formed so that one side of the channel segments includes one of the thermal conducting layers. This allows the fluids in the channel segments to have direct contact with the conducting layer that is at the desired temperature. The insulating layer channels are "adjacent" the conducting layers whether or not they are in direct contact with the conducting layer.

Forming channel segments in the insulating layer is easier and less expensive than forming the channel segments in the conducting layers. The insulating layers are typically made from a plastic or polymeric material and the channel segments can be easily formed in them by injection molding techniques. This eliminates the expensive etching or other processes described above which can be used to form the channels in the conducting layers.

Figure 21A:
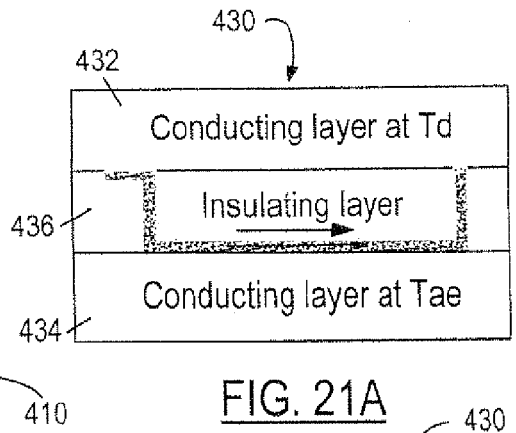
FIGS. 21A and 21B illustrate a two-temperature device in which fluid channels are formed in an insulating layer.
Figure 21B:
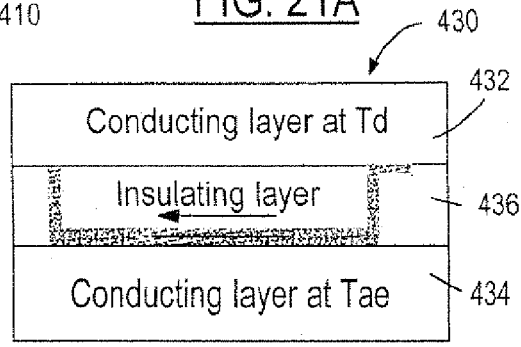

FIGS. 21A and 21B illustrate a two-layer thermal cycling device 430 which has channel segments in the insulating layer. The device has a first conducting (denaturation) layer 432, a second conducting (annealing/extension) layer 434, and an insulating layer 436. The layer 432 is held at the denaturation temperature, while the layer 434 is held at the combined annealing extension temperature. The fluid path in the device 430 alternatives from left to right, as shown in FIG. 21A and then from right to left as shown in FIG. 21B.

The device shown in FIG. 20 also is a "folded channel" device, that is the extension channel segments exist in two planes on alternate sides of the conducting layer 406. This same principle can be applied to make the thermal cycling device smaller since it is often desirable to have the extension layer much longer than the denaturation and annealing layers. By using both sides of the extension layer, the device can be made more compact.

It is also possible to have the channel "fold back" and provide two or more channel segments in either the annealing or denaturing layer. Similar savings in size and cost could be realized. In addition, there could be multiple folds in any of the layers making the device more compact.

Figure 22:
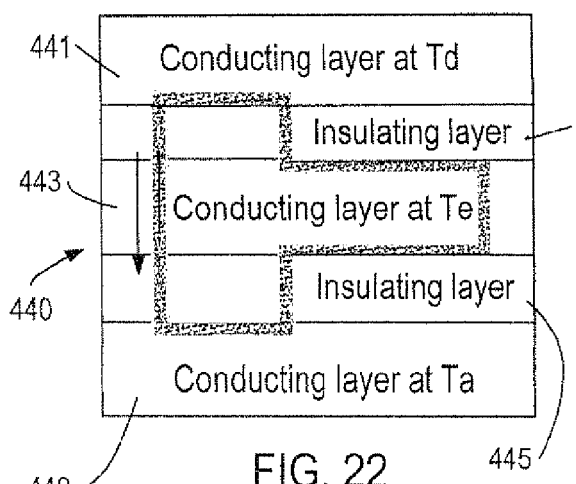
FIG. 22 schematically illustrates another three-temperature device in which fluid channels are positioned in both sides of the extension layer.
Figure 23:
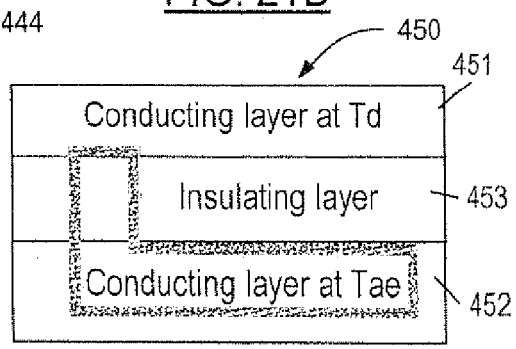
FIG. 23 schematically illustrates another two-temperature device in which fluid channels are positioned in both sides of the annealing/extension layer.

FIGS. 20, 22 and 23 illustrate three devices using the "folding channel" principle. In FIG. 20, the device 400, which has three conducting layers, has a folded extension channel, with part of it residing in insulating layer 408 and the other part in insulating layer 410. In FIG. 22, the device 440, which has three conducting layers, again has a folded extension layer, with part of it residing in the upper face of conducting layer 443 and the other part in the lower face of conducting layer 443. In FIG. 23, the device 450, which has two conducting layers, has a folding annealing-extension channel, with part of it residing within conducting layer 452 and part of it residing on the top surface of conducting layer 452.

Figure 24:
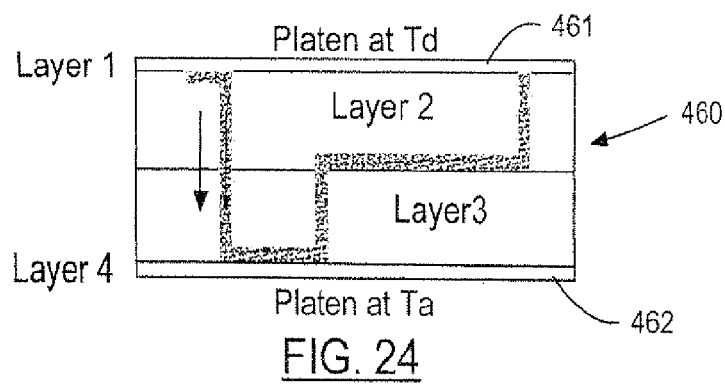
FIG. 24 schematically illustrates another three-temperature device in accordance with the present invention.

In the multiple layer devices described above, the layers could be of the same or dissimilar materials. FIGS. 24 and 25A/25B depict two devices in which the layers are made of homogeneous materials.

In FIG. 24, the device 460 is a three temperature device using homogeneous materials. The external platens 461 and 462 take the place of the conducting layers 441 and 442 which are present in FIG. 22. The layers 1 and 4 (461 and 462) are sufficiently thin such that there is only a negligible temperature drop across them.

FIGS. 25A and 25B depict a two-temperature device 470 using homogenous materials. Consecutive cycles are shown in FIGS. 25A and 25B. Layers 1 (471) and 3 (472) are sufficiently thin such that there is a negligible temperature drop across them.

FIGS. 26 and 27 depict a thermal cycling device 480, with FIG. 27 being an exploded view thereof. The device 480 includes at least one conducting layer 481 which has a pair of tabbed connectors 482A and 482B. The tabbed connectors are used to connect the thermal heating and heat sinking sources to the conducting layer 481. Layer 481 is a conducting denaturation layer and is equipped with tabbed connectors ("tabs") that provide a large surface area over which to conduct heat.

FIG. 28 illustrates a two-temperature device 490 which has a clear cover window (glass layer 491) over the denaturation layer 402. The clear window layer allows real time PCR with detection on the annealing/extension side of the thermal cycling device 490. With two-temperature devices, real time detection during annealing/extension could be advantageous because more channel area 493 is exposed, as shown in FIG. 28.

While the invention has been described in connection with one or more embodiments, it should be understood that the invention is not limited to those embodiments. On the contrary, the invention is intended to cover all alternatives, modifications, and equivalents, as may be included within the spirit and scope of the appended claims.

What is claimed is:

1. A three-layer apparatus for performing a polymerase chain reaction comprising:
    a first thermally conductive layer;
    a second thermally conductive layer;
    a third thermally conductive layer;
    a first insulating layer positioned between said first and second thermally conductive layers;
    a second insulating layer positioned between said second and third thermally conductive layer; and
    a continuous channel having channel segments formed within said first insulating layer, said second thermally conducting layer and said second insulating layer;
    said first, second and third thermally conductive layers being substantially the same size and being positioned one on top of the other forming a multi-layer apparatus.

2. The three-layer apparatus as described in claim 1 wherein one of said channel segments in said first insulating layer is adjacent to said first thermally conductive layer and one of said channel segments in said second insulating layer is adjacent to said third thermally conductive layer.

3. The three-layer apparatus as described in claim 1 wherein said first thermally conductive layer is a denaturing layer, said third thermally conductive layer is an annealing layer, and said second thermally conductive layer is an extension layer.

4. The three-layer apparatus as described in claim 3 wherein at least one of said channel segments extends for a first direction in its respective layer and then reverses itself and extends in the opposite direction in the same layer before proceeding to another layer.

5. The three-layer apparatus as described in claim 4 wherein said at least one of said channel segments extend for said first direction on one side of its respective layer and then reverses itself and extends in said opposite direction on the opposite side of said same layer before proceeding to another layer.

6. The three-layer apparatus as described in claim 5 wherein said respective layer is an extension layer and said at least one of said channel segments is at least partially formed in an insulating layer.

7. The three-layer apparatus as described in claim 1 further comprising at least one temperature source for maintaining said first thermally conductive layer at a first temperature and for maintaining said third thermally conductive layer at a second temperature lower than said first temperature.

8. A two-layer apparatus for performing a polymerase chain reaction comprising:
    a first conducting layer;
    a second conducting layer;
    an insulating layer positioned between said first and second conducting layers;
    a continuous channel having a plurality channel segments, at least one of said channel segments positioned in said insulating layer;
    wherein said first conducting layer is positioned on top of said second conducting layer, and said first and second conducting layers are substantially coextensive with one another.

9. The two-layer apparatus as described in claim 8 wherein at least one channel segment is adjacent to said first conducting layer and at least one channel segment is positioned adjacent to said second conducting layer.

10. The two-layer apparatus as described in claim 8 further comprising at least one temperature source for maintaining said first and second conducting layers at prespecified temperatures.

11. The two-layer apparatus as described in claim 10 wherein one of said conducting layers has a tab member thereon for connecting to said temperature source.

12. The two-layer apparatus as described in claim 8 wherein at least one channel segment is a denaturing segment, and at least one channel segment is an annealing-extension segment.

13. The two-layer apparatus as described in claim 12 wherein at least two channel segments extend for a first direction in one of said layers and then reverse themselves and extend in the opposite direction in said same layer.

14. The two-layer apparatus as described in claim 12 wherein at least two annealing or denaturing segments are present in the same layer or adjacent the same layer.

15. A method for performing a polymerase chain reaction comprising:
 (a) introducing a sample into a three-layer apparatus, said three-layer apparatus comprising:
  a first thermally conductive layer;
  a second thermally conductive layer;
  a third thermally conductive layer;
  said first, second and third thermally conductive layers being substantially the same size and being positioned one on top of the other forming a three-layer apparatus;
  a first insulating layer positioned between said first and second thermally conductive layers;
  a second insulating layer positioned between said second and third thermally conductive layer; and
  at least one temperature source for maintaining said first thermally conductive layer at a first temperature and for maintaining said third thermally conductive layer at a second temperature lower than said first temperature;
  a continuous channel having channel segments formed within said first insulating layer, said second thermally conducting layer and said second insulating layer;
 (b) performing a first portion of a cycle in a first channel segment at a first temperature;
 (c) moving the sample to another layer;
 (d) thereafter, performing a second portion of the cycle in a second channel segment at a second temperature;
 (e) moving the sample to a second channel segment;
 (f) thereafter, performing a third portion of a cycle in a third channel segment at a third temperature; and
 (g) repeatedly performing the first portion, the second portion and the third portion for a predetermined number of cycles to perform the reaction.

16. A method for performing a polymerase chain reaction comprising:
 (a) introducing a sample into a two-layer apparatus comprising:
  a first conducting layer;
  a second conducting layer;
  said first and second conducting layer being substantially the same size and being positioned one on top of the other forming a two layer apparatus;
  an insulating layer positioned between said first and second conducting layers; and
  a continuous channel having at least one channel segment within said insulating layer;
 (b) performing a first portion of a cycle in a first channel segment at a first temperature;
 (c) moving the sample to a second channel segment;
 (d) thereafter, performing a second portion of the cycle in said second channel segment at a second temperature;
 (e) moving the sample to a third channel segment;
 (f) thereafter, performing a third portion of a cycle in said third channel segment at a third temperature; and
 repeatedly performing the first portion, the second portion and the third portion for a predetermined number of cycles to perform the reaction.

17. A multi-layer apparatus for performing a polymerase chain reaction comprising:
 a first thermally conductive layer;
 a second thermally conductive layer;
 a third thermally conductive layer;
 a first insulating layer positioned between said first and second thermally conductive layers;
 a second insulating layer positioned between said second and third thermally conductive layers;
 a first heat source for maintaining said first thermally conductive layer at a first temperature; a second heat source for maintaining said third thermally conductive layer at a second temperature lower than said first temperature;
 said first, second and third thermally conductive layers being substantially the same size and being positioned one on top of the other forming a multi-layer apparatus; and
 a continuous channel formed in said multi-layer apparatus for performing a polymerase chain reaction, said channel having a first channel segment in said first insulating layer adjacent said first thermally conductive layer, and a second channel segment in said first insulating layer adjacent said second thermally conductive layer, a third channel segment in said second insulting layer adjacent said second thermally conductive layer, and a fourth channel segment in said second insulting layer adjacent said third thermally conductive layer.

18. A two-layer apparatus for performing a polymerase chain reaction comprising:
 a first thermally conductive layer;
 a second thermally conductive layer;
 an insulating layer positioned between said first and second thermally conductive layers;
 said first and second thermally conductive layers being substantially the same size and being positioned one on top of the other forming a multi-layer apparatus; and
 a continuous channel formed in said multi-layer apparatus for performing a polymerase chain reaction, said channel having at least one of the channel segments positioned in the insulating layer.

19. A two-layer apparatus as described in claim 18 wherein all of the channel segments are positioned in the insulating layer.

20. A multi-layer PCR device for processing a nucleic acid sample comprising:
 at least two thermally conductive layers;
 at least one insulating layer;
 said thermally conductive layers and said insulating layer being substantially the same size and being positioned one on top of the other forming a multi-layer device; and
 a continuous channel in said multi-layer device for circulation and processing of a nucleic acid sample.

21. The device as described in claim 20 further comprising heating sources for heating said thermally conductive layers.

22. The device as described in claim 20 wherein said continuous channel comprises a plurality of channel segments and wherein at least one channel segment is located in said insulating layer.

23. The device as described in claim 22 wherein all of said channel segments are located in said insulating layer.

24. The device as described in claim 20 wherein three thermally conductive layers are provided.

25. The device as described in claim 20 wherein two insulating layers are provided.

26. The device as described in claim 20 wherein three thermally conductive layers and two insulating layers are provided.

27. The device as described in claim 26 wherein said continuous channel has a plurality of channel segments and at least one channel segment is located in one of said insulating layers.

28. The device as described in claim 26 wherein said continuous channel has a plurality of channel segments and at least one channel segment is located in each of said insulating layers.

29. The device as described in claim 26 wherein said continuous channel has a plurality of channel segments and a plurality of said channel segments are located in said insulating layers.

30. The device as described in claim 26 wherein each of said two insulating layers is positioned between two of said thermally conductive layers.

31. The device as described in claim 20 wherein one insulating layer and two thermally conductive layers are provided, and wherein said insulating layer is positioned between said two thermally conductive layers.

32. The device as described in claim 31 wherein said continuous channel comprises a plurality of channel segments and wherein one of said channel segments is located in said insulating layer adjacent to one of said thermally conductive layers.

33. The device as described in claim 26 wherein said first thermally conductive layer is a denaturing layer, said third thermally conductive layer is an annealing layer, and said second thermally conductive layer is an extension layer.

34. The device as described in claim 22 wherein at least one of said channel segments extends for a first direction in its respective layer and then reverses itself and extends in the opposite direction in the same layer before proceeding to another layer.

35. The device as described in claim 30 wherein said continuous channel comprises a plurality of channel segments and wherein one of said channel segments is located in said first insulating layer adjacent to said first thermally conductive layer and one of said channel segments is located in said second insulating layer adjacent to said third thermally conductive layer.

36. The device as described in claim 30 wherein said first thermally conductive layer is a denaturing layer, said third thermally conductive layer is an annealing layer, and said second thermally conductive layer is an extension layer.

37. The device as described in claim 35 wherein at least one of said channel segments extends for a first direction in its respective layer and then reverses itself and extends in the opposite direction in the same layer before proceeding to another layer.

* * * * *

UNITED STATES PATENT AND TRADEMARK OFFICE
Certificate

Patent No. 8,043,849 B2                                   Patented: October 25, 2011

On petition requesting issuance of a certificate for correction of inventorship pursuant to 35 U.S.C. 256, it has been found that the above identified patent, through error and without any deceptive intent, improperly sets forth the inventorship.
   Accordingly, it is hereby certified that the correct inventorship of this patent is: Joel W. Grover, Pittsford, NY (US); and Robert Juncosa, Fairport, NY (US).

Signed and Sealed this Seventeenth Day of July 2012.

Michael A. Marcheschi
Supervisory Patent Examiner
Art Unit 1775
Technology Center 1700